United States Patent
Fukuda et al.

(10) Patent No.: US 9,238,814 B2
(45) Date of Patent: Jan. 19, 2016

(54) RIBOZYME FOR IDENTIFYING MODIFICATION ON RNA SEQUENCE AND RNA CLEAVAGE METHOD USING SAME

(75) Inventors: Masatora Fukuda, Fukuoka (JP); Masanobu Deshimaru, Fukuoka (JP); Kei Kurihara, Fukuoka (JP)

(73) Assignee: Fukuoka University, Fukuoka (JP)

( * ) Notice: Subject to any disclaimer, the term of this patent is extended or adjusted under 35 U.S.C. 154(b) by 51 days.

(21) Appl. No.: 14/118,562

(22) PCT Filed: May 19, 2012

(86) PCT No.: PCT/JP2012/062878
§ 371 (c)(1),
(2), (4) Date: Nov. 19, 2013

(87) PCT Pub. No.: WO2012/161144
PCT Pub. Date: Nov. 29, 2012

(65) Prior Publication Data
US 2014/0228556 A1 Aug. 14, 2014

Related U.S. Application Data

(60) Provisional application No. 61/488,345, filed on May 20, 2011.

(51) Int. Cl.
*C12N 15/113* (2010.01)
*C12Q 1/68* (2006.01)
*C12N 15/11* (2006.01)

(52) U.S. Cl.
CPC ............ *C12N 15/113* (2013.01); *C12N 15/111* (2013.01); *C12Q 1/6816* (2013.01); *C12N 2310/121* (2013.01); *C12N 2320/10* (2013.01)

(58) Field of Classification Search
USPC .............. 435/6.1, 6.11, 91.1, 91.31, 91, 1.31; 536/23.1, 24.5, 25.3
See application file for complete search history.

(56) References Cited

PUBLICATIONS

Thomson et al, Nucleic Acids Res., vol. 24, No. 22, pp. 4401-4406 (1996).*
Dawson et al (Nucleic Acids Res., vol. 28, No. 20, pp. 4013-4020 (2000).*
Kore et al, Nucleic Acids Res., vol. 26, No. 18, pp. 4116-4120 (1998).*
Tang, J. and Breaker, R. R., Examination of the catalytic fitness of the hammerhead ribozyme by in vitro selection, RNA, 1997, vol. 3, p. 914-925.; Cited in International Search Report.
Pan, W. H. et al., Rapid identification of efficient target cleavage sites using a hammerhead ribozyme library in an iterative manner, Molecular Therapy, Jan. 2003, vol. 7 No. 1, pp. 129-139.; Cited in International Search Report.
Thomson, J. B. et al., In vitro selection of hammerhead ribozymes containing a bulged nucleotide in stem II, Nucleic Acids Research, 1996, vol. 24 No. 22, pp. 4401-4406.; Cited in International Search Report.
Moshiri, H. and Salavati, R., A fluorescence-based reporter substrate for monitoring RNA editing in trypanosomatid pathogens, Nucleic Acids Research, 2010, col. 38 No. 13, e138, pp. 1-13.; Cited in International Search Report.
Scott, W.G. et al., The crystal structure of an all-RNA hammerhead ribozyme : a proposed mechanism for NRA catalytic cleavage, Cell, Jun. 1995, vol. 81, pp. 991-1002; Cited in International Search Report.
Eckstein, F. et al., In vitro selection of hammerhead ribozyme sequence variants, Chembiochem, 2001, vol. 2, pp. 629-635.; Cited in International Search Report.
Vaish, N. K. et al., In vitro selection of a purine nucleotide-specific hammerhead-like ribozyme, Proc. Natl. Acad. Sci. USA, Mar. 1998, vol. 95, pp. 2158-2162; Cited in International Search Report.
Maas, S. et al., A-to-I RNA editing and human disease, RNA Biology, Jan./Feb. Mar. 2006, vol. 3 No. 1, pp. 1-9.; Cited in International Search Report and Specification.
Werry, T. D. et al., RNA editing of the serotonin 5HT2C receptor and major effects on cell signaling, pharmacology and brain function, Pharmacology & Therapeutics, 2008, vol. 119, pp. 7-23.; Cited in International Search Report.
Iwamoto, K. and Kato, T., RNA editing of serotonin 2C receptor and major mental disorders, Yakugaku Zasshi, 2008, vol. 128 No. 4, pp. 521-525.; Cited in International Search Report.
Nishimoto, Y. et al., Determination of editors at the novel A-to-I editing positions, Neuroscience Research, 2008, vol. 61, pp. 201-206.; Cited in International Search Report.
Sowden, M.P. et al., Apolipoprotein B RNA sequence 3' of the mooring sequence and cellular sources of auxiliary factors determine the location and extent of promiscuous editin, Nucleic Acids Research, 1998, vol. 26 No. 7, pp. 1644-1652.; Cited in International Search Report.
Yamanaka, S. and Iwao, H., RNA editing, Tanpakusitsukakusankouso, 1997, vol. 42 No. 6, pp. 803-811.; Cited in International Search Report.
Maas, S. and Rich, A. 2000. Changing genetic information through RNA editing. Bioessays 22(9): 790-802; Cited in Specification.
Bass, B. L. 2002. RNA editing by adenosine deaminases that act on RNA. Annu Rev BioChemical Formula 71:817-846; Cited in Specification.
Farajollahi, S. and Maas, S. 2010. Molecular diversity through RNA editing: a balancing act. Trends Genet 26(5):221-230; Cited in Specification.
Nishikura, K. 2010. Functions and regulation of RNA editing by ADAR deaminases. Annu Rev BioChemical Formula 79: 321-349.; Cited in Specification.
Pullirsch, D. and Jantsch, M. F. 2010. Proteome diversification by adenosine to inosine RNA editing. RNA Biol 7(2):205-212.; Cited in Specification.

(Continued)

*Primary Examiner* — Jane Zara
(74) *Attorney, Agent, or Firm* — Rankin, Hill & Clark LLP

(57) ABSTRACT

The hammerhead ribozyme according to the present invention produces a hammerhead ribozyme—target RNA construct by base-pairing with an edited target RNA, and an editing recognition site of the hammerhead ribozyme cleaves the modification site by forming a base pair with the target RNA modification site. The cleavage of the modification site is expected to be applicable to the research and development of new drugs that can be used to prevent or treat diseases caused by the edited target RNA.

1 Claim, 21 Drawing Sheets

(56) References Cited

PUBLICATIONS

Burns, C. M., Chu, H., Rueter, S. M., Hutchinson, L. K., Canton, H., Sanders-Bush, E., and Emeson, R. B. 1997. Regulation of serotonin-2C receptor G-protein coupling by RNA editing. Nature 387(6630): 303-308; Cited in Specification.

Sommer, B., Kohler, M., Sprengel, R., and Seeburg, P. H. 1991. RNA editing in brain controls a determinant of ion flow inglutamate-gated channels. Cell 67(1): 11-19; Cited in Specification.

Werry, T. D., Loiacono, R., Sexton, P. M., and Christopoulos, A. 2008. RNA editing of the serotonin 5HT2C receptor and its effects on cell signaling, pharmacology and brain function. Pharmacol Ther 119(1): 7-23.; Cited in Specification.

Terada, S., et al., Fukuoka University science reports 40(1) 116-123 (2010); Cited in Specification.

Higuchi, M., Single, F. N. Kohler, M., Sommer, B., Sprengel, R., and Seeburg, P. H. 1993. RNA editing of AMPA receptor subunit GluR-B: a base-paired intron-exon structure determines position and efficiency. Cell 75(7):1361-1370.; Cited in Specification.

Blanc, V. and Davidson, N. O. 2003. C-to-U RNA editing: mechanisms leading to genetic diversity. J Biol Chemical Formula 278(3): 1395-1398.; Cited in Specification.

Wang, A. B., Liu, D. P., and Liang, C. C. 2003. Regulation of human apolipoprotein B gene expression at multiple levels. Exp Cell Res 290(1):1-12.; Cited in Specification.

Levanon, E. Y., Hallegger, M., Kinar, Y., Shemesh, R., Djinovic-Carugo, K., Rechavi, G., Jantsch, M. F., and Eisenberg, E. 2005. Evolutionarily conserved human targets of adenosine to inosine RNA editing. Nucleic Acids Res 33(4): 1162-1168; Cited in Specification.

Gommans, W. M., Tatalias, N. E., Sie, C. P., Dupuis, D., Vendetti, N., Smith, L., Kaushal, R., and Maas, S. 2008. Screening of human SNP database identifies recoding sites of A-to-I RNA editing. RNA 14(10): 2074-2085; Cited in Specification.

Li, J. B., Levanon, E. Y., Yoon, J. K., Aach, J., Xie, B., Leproust, E., Zhang, K., Gao, Y., and Church, G. M. 2009. Genome-wide identification of human RNA editing sites by parallel DNA capturing and sequencing. Science 324(5931): 1210-1213; Cited in Specification.

Tedeschi, L., Lande, C., Cecchettini, A., and Citti, L. 2009. Hammerhead ribozymes in therapeutic target discovery and validation. Drug Discov Today 14(15-16): 776-783.; Cited in Specification.

Kore, A. R., Vaish, N. K., Kutzke, U., and Eckstein, F. 1998. Sequence specificity of the hammerhead ribozyme revisited; the NHH rule. Nucleic Acids Res 26(18): 4116-4120; Cited in Specification.

Scherr, M., Grez, M., Ganser, A., and Engels, J. W. 1997. Specific hammerhead ribozyme-mediated cleavage of mutant N-ras mRNA in vitro and ex vivo. Oligoribonucleotides as therapeutic agents. J Biol Chemical Formula 272(22):14304-14313; Cited in Specification.

Lewin, A. S., Drenser, K. A., Hauswirth, W. W., Nishikawa, S., Yasumura, D., Flannery, J. G., and LaVail, M. M. 1998. Ribozyme rescue of photoreceptor cells in a transgenic rat model of autosomal dominant retinitis pigmentosa. Nat Med 4(8): 967-971; Cited in Specification.

Dawson, P. A. and Marini, J. C. 2000. Hammerhead ribozymes selectively suppress mutant type I collagen mRNA in osteogenes is imperfect a fibroblasts. Nucleic Acids Res 28(20): 4013-4020.; Cited in Specification.

International Search Report dated Jul. 24, 2012 filed in PCT/JP2012/062878.

* cited by examiner

FIG. 1 RNA EDITING AND 2'-O-METHYLATION ON HTR2C mRNA (SEQ ID NO:68)

FIG. 7
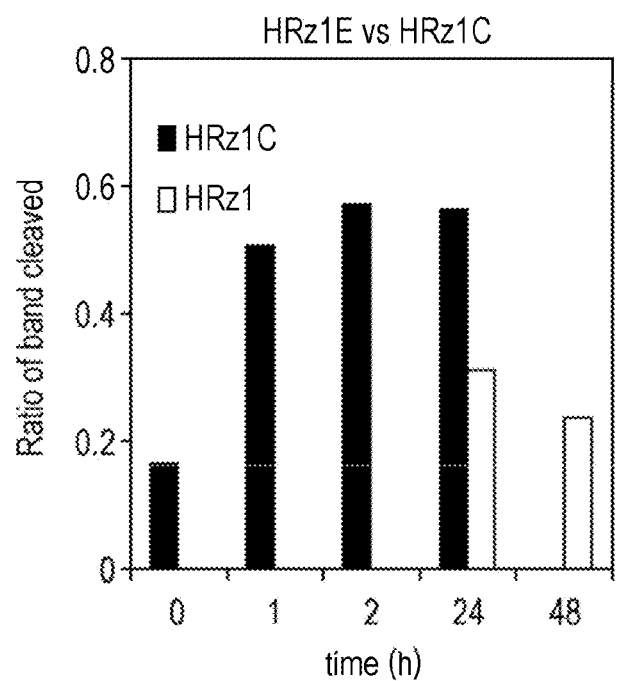
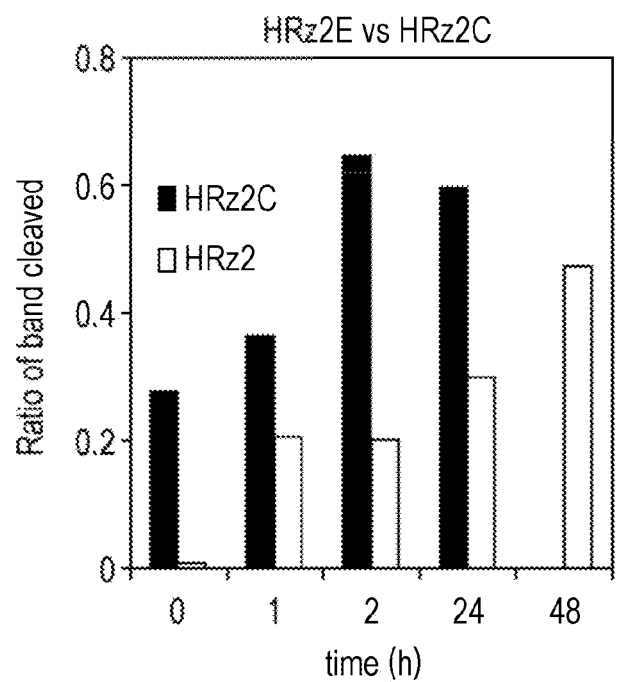

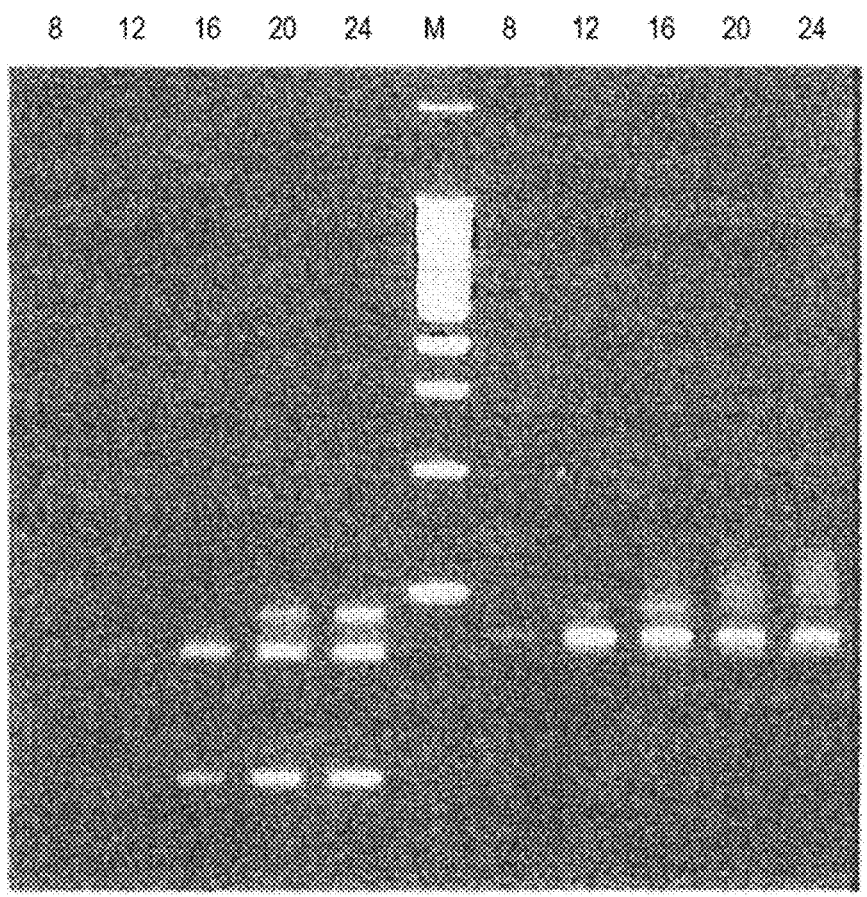

FIG. 14

| | | |
|---|---|---|
| Library H2 | GGCUAUGCUCA NNNN AUAGGA NNNNNNNNNNNNNNNNNNNNNNNN UACGUAUGCUACAUACC | (SEQ ID NO:46) |
| H2-8-20 | GGCUAUGCUCA CCGA AUAGGA CACACAACGUGAGUACCAGG UACGUAUGCUACAUACC | (SEQ ID NO:47) |
| H2-8-24 | GGCUAUGCUCA GAUG AUAGGA CCCCAACUCGGCACCUACU// GACGUAUGCUACAUACC | (SEQ ID NO:48) |
| H2-8-09 | GGCUAUGCUCA CAUA AUAGGA CUAAUUGUCAAACCUUUUAUGU GACGUAUGCUACAUACC | (SEQ ID NO:49) |
| H2-8-06 | GGCUAUGCUCA GACC CUAGGA ACCAAACAAAUACCGAAACGUCU GACGUAUGCUACAUACC | (SEQ ID NO:50) |
| H2-8-15 | GGCUAUGCUCA UGGC AGAGGA GACACCAAACUACCGACACACCAU GACGUAUGCUACAUACC | (SEQ ID NO:51) |
| H2-8-23 | GGCUAUGCUCA CCAC AAAGGA AAACGAACUUCGCCCCUACCCCGU GACGUAUGCUACAUACC | (SEQ ID NO:52) |
| H2-8-12 | GGCUAUGCUCA CCUG AUAGAA CAAAAUGCACCACAACCCCACGU/ GACGUAUGCUACAUACC | (SEQ ID NO:53) |
| H2-8-19 | GGCU/UGCUCA ACCC AGAGGA AGAGCAAAAACAUACGACGAUCUG UGCGUAUGCUACAUACC | (SEQ ID NO:54) |
| H2-8-07 | GGCUAUGCUCA UGAA AUAGGA CAAACAAACCUCACCAUUUCAUGA UGCGUAUGCUACAUACC | (SEQ ID NO:55) |
| H2-8-14 | GGCUAUGCUCA GGUU AUAGGA CCCACCAAAAGAAACUAGACCUGA UGCGUAUGCUACAUACC | (SEQ ID NO:56) |
| H2-8-16 | GGCUAUGCUCA CACC AUAGGA CCAACCAAACGAACCGAAGUGUGA UGCGUAUGCUACAUACC | (SEQ ID NO:57) |
| H2-8-02 2/18 | GGCUAUGCUCA GACA AAAGGA CAAAACUACACCCAAACCCUG/// AGCGUAUUGCUACAUACC (SEQ ID NO:58) | |
| H2-8-05 | GGCUAUGCUCA GAUG AUAAGA CAAAACCCGAAUCCUG//////// AGCGUAUUGCUACAUACC | (SEQ ID NO:59) |
| H2-8-03 2/10 | GGCUAUGCUCA CCAA AUAAGA AACCAAAACCUAAAAGUG////// AGCGUAUUGCUACAUACC (SEQ ID NO:60) | |
| H2-8-04 | GGCUAUGCUCA CCAA AUAAGA AACCAAAACCUAAAAAUG///// AGCGUAUUGCUACAUACC | (SEQ ID NO:61) |
| H2-8-10 | GGCUAUGCUCA CCCAAAUAAGA AACCAAAACCUAAAAGUG////// AGCGUAUUGCUACAUACC | (SEQ ID NO:62) |

FIG. 15

| | | |
|---|---|---|
| Library H2 | GGCUAUGCUCA NNNN AUAGGA NNNNNNNNNNNNNNNNNNNNNNNN UACGUAUGCUACAUACC | (SEQ ID NO:46) |
| H2-01 | GGCUAUGCUCA GGAA AUAAGA ACUAAAAAUCCCAAAAACCUGAG UACGUAUGCUACAUACC 7/36 | (SEQ ID NO:63) |
| H2-06 | GGCUAUGCUCA CCUA AUAGAA AAUCCCAAAACAUCUAGAUAAAGU GACGUAUGCUACAUACC 3/36 | (SEQ ID NO:64) |
| H2-37 | GGCUAUGCUCA GGAA AUAGGA GCUGACAAAGCAAACCUACCUGAG UACGUAUGCUACAUACC 2/36 | (SEQ ID NO:65) |

FIG. 19
A
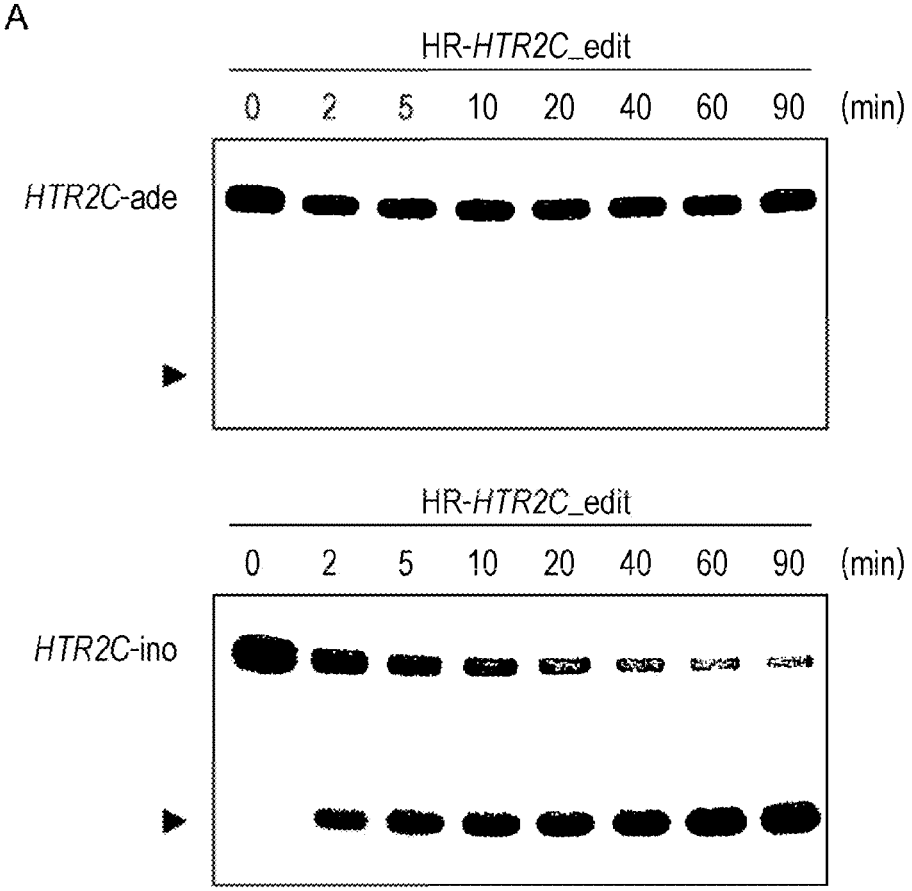
B
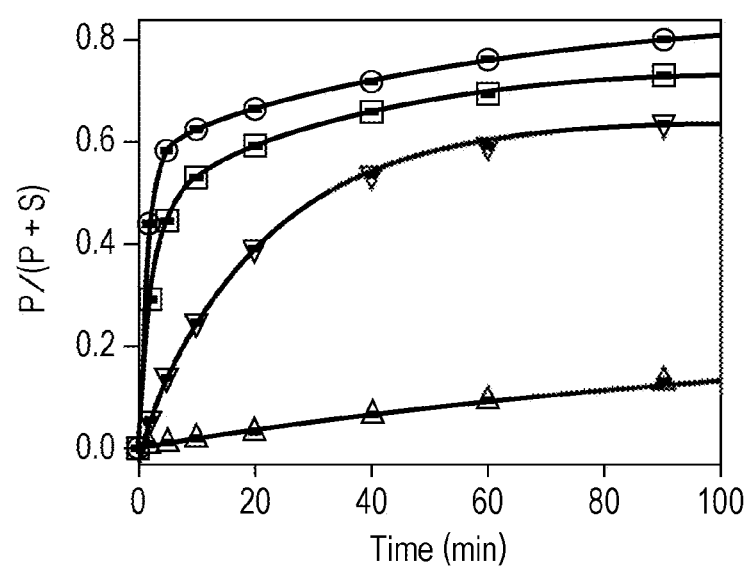

FIG. 20
A
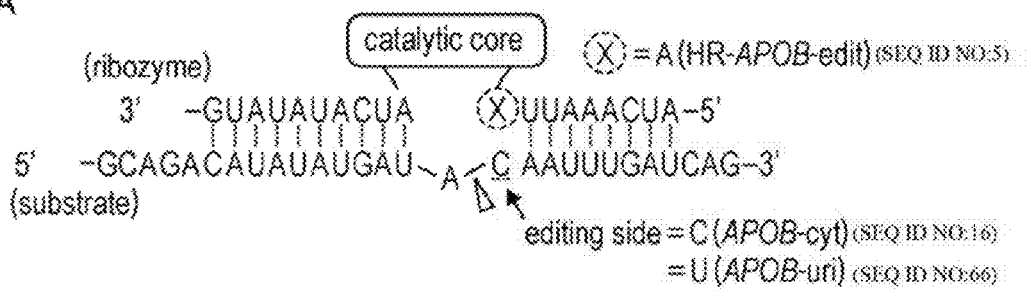
B
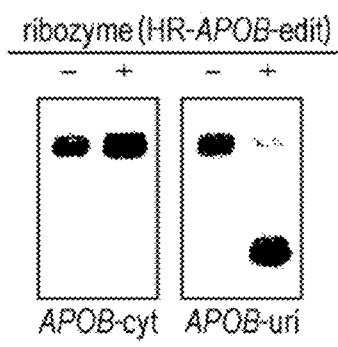
C
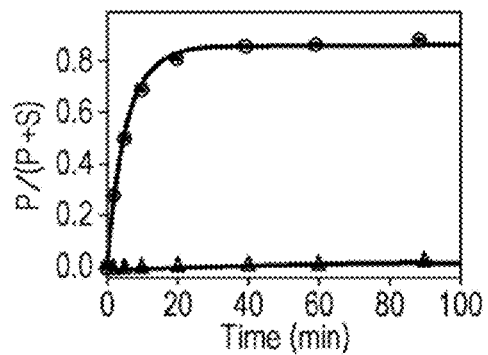

*FIG. 22*
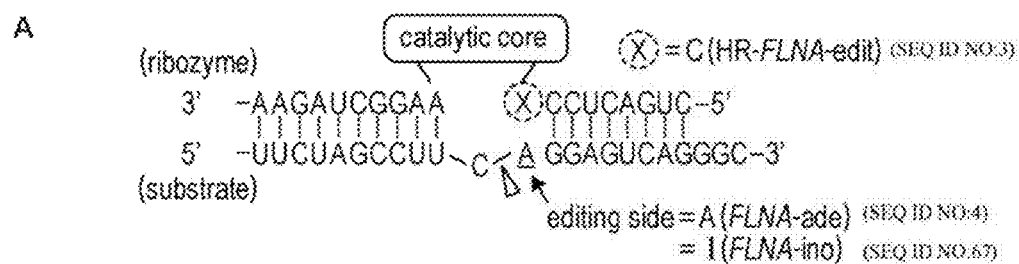
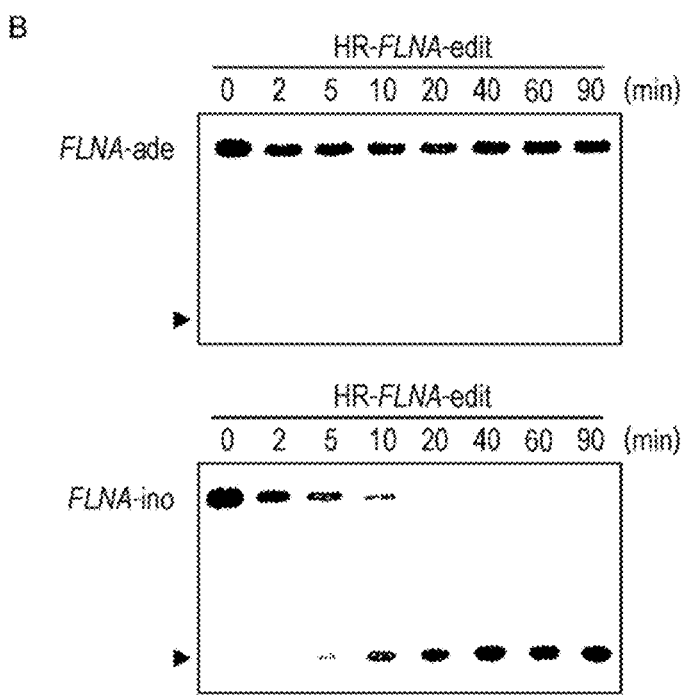
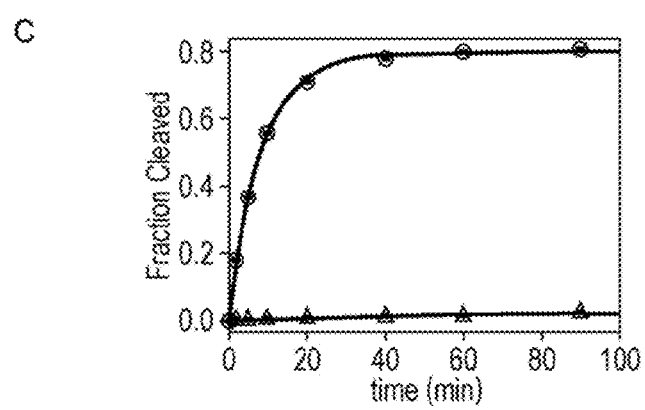

FIG. 23A
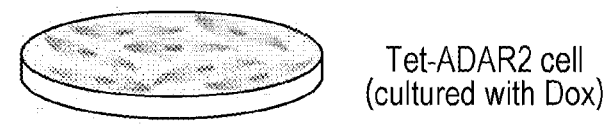
Tet-ADAR2 cell (cultured with Dox)
▼ Extraction of total RNA
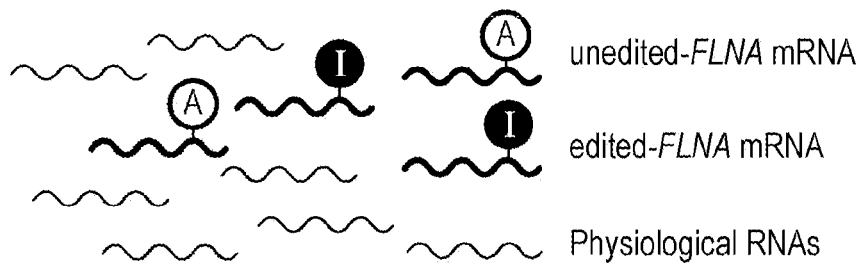
unedited-*FLNA* mRNA
edited-*FLNA* mRNA
Physiological RNAs
▼ Cleavage reaction
▼ RT-PCR
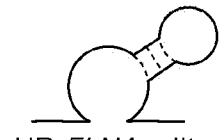
HR-*FLNA*-edit
▼ Direct Sequencing
Quantifying the editing ratio

RIBOZYME FOR IDENTIFYING MODIFICATION ON RNA SEQUENCE AND RNA CLEAVAGE METHOD USING SAME

TECHNICAL FIELD

This application claims priority on U.S. Provisional Application No. 61/488,345 filed on May 20, 2011. The present invention relates to a ribozyme for identifying modification on an RNA sequence and an RNA cleavage method using the same. More specifically, the present invention relates to a hammerhead ribozyme for identifying modification on an RNA sequence by RNA editing and the like and an RNA cleavage method using the same.

BACKGROUND ART

It is known that RNA in a living organism is chemically modified, and noncoding RNA such as rRNA and tRNA is functionalized by modification. Meanwhile, mRNA is also modified and, for example, modification such as RNA editing such as A-to-I editing in which adenosine (A) is substituted by inosine (I) in the nucleotides of mRNA and C-to-U editing in which cytosine (C) is substituted by uracil (U) is known.

Among these, RNA editing is a mechanism to convert genetic information after transcription and a phenomenon to alter the base at a specific site in the base sequence of pre-mRNA generated by transcription of a gene into another base by enzyme action, and appears in various forms such as insertions, deletions or substitutions of bases (Non-Patent Document 1). This phenomenon is generally a mechanism programmed in living organisms to change gene products depending on changes in physiological conditions and environments. In higher eukaryotes, it is believed that A-to-I editing in which the adenosine (A) base at a specific site in pre-mRNA is substituted by the inosine (I) base by the action of adenosine deaminase (ADAR) has a physiologically important meaning (Non-Patent Document 2). When A-to-I base substitution occurs in an mRNA sequence encoding a protein, since the inosine (I) is read as guanosine by ribosomes during translation, codons are changed, thereby genetic information is converted and a protein having a function different from that of the original one is generated.

As the most researched RNA precursors about A-to-I editing in coding RNA, there are mentioned serotonin 2C receptor (HTR2CR) and glutamate receptor subunit B (GRIA2) (Non-Patent Document 3).

Serotonin 2C receptor (HTR2CR) is a seven-transmembrane G protein-coupled receptor mediating neural signaling in the brain by serotonin and is believed to be deeply involved in emotion control, and is known to be subjected to RNA editing (A-to-I editing) in which 5 adenosines (A) at the A to E sites on HTR2C pre-mRNA are substituted by inosine (I) by double-stranded RNA-specific adenosine deaminase (ADAR) (Non-Patent Document 4, FIG. 1).

Even in normal healthy people, adenosine (A) bases at the A site to the E site in HTR2CR mRNA are altered into the inosine (I) base with proper frequency by A-to-I editing by the catalytic action of enzymes ADAR1 and ADAR2. Consequently, it is reported that emotion is normally controlled in normal healthy people, while the regulation is broken in patients with depression and suicides. It is believed that the defect in RNA editing in serotonin 2C receptor (HTR2CR) is involved in functional psychoses such as depression, schizophrenia and autism; however, a mechanism to control normal regulation has not yet been revealed.

As shown in FIG. 2, serotonin 2C receptor (HTR2CR), when serotonin is bound to the extracellular loop of HTR2CR, transmits impulses to coupled G protein, then causes changes in properties of nerve cells via intracellular signal transduction pathway and eventually controls cerebral functions such as memory, learning and emotion. When serotonin 2C receptor (HTR2CR) is subjected to RNA editing, the amino acid sequence in the G protein-binding region of a receptor protein is changed and the signal transduction ability of the receptor is changed. In HTR2CR, up to 24 types (mainly 8 types) of receptor proteins with different amino acid sequences and different transmitting abilities are generated from a single gene by combining sites subjected to RNA editing (shown by solid-white letters in the drawing) among the base sequence of HTR2CR and amino acids to be encoded (Non-Patent Documents 4 and 5).

In the pre-mRNA of glutamate receptor subunit B (GRIA2), desensitization kinetics of the receptor and an ion channel, Ca2++ permeability, are controlled by RNA editing (Non-Patent Document 6).

As another form of RNA modification by substitution, C-to-U editing in which cytosine (C) is substituted by uracil (U) and cytosine is converted to uridine by deamination is known (Non-Patent Document 7). It is reported that the nucleus transcriptional body encoding intestinal apolipoprotein B (ApoB) is subjected to C-to-U RNA editing to convert a CAA codon to a UAA stop codon and a shorter protein than that before editing is generated (Non-Patent Document 8).

As described above, RNA editing such as A-to-I editing and C-to-U editing is involved in an important mechanism to control genetic adaptability by generating a protein different from a protein to be generated when editing does not occur. RNA modification by substitution in a coding region plays a definitive role in biological process control, and thus the development of abnormal modification is a cause of a serious disease (Non-Patent Document 9), and, in particular, the relation of RNA modification by substitution to mental disorders such as schizophrenia, bipolar disorder and major depressive disorder attracts attention.

Along with RNA precursors of serotonin 2C receptor (HTR2C) and glutamate receptor subunit B (GRIA2), particularly, γ-amino butyric acid (GABA) receptor, a receptor deeply involved in the neuropsychiatric function of the central nervous system such as potassium channels, ion channels, and other targets of RNA editing in sequences encoding proteins of other proteins have been identified recently (Non-Patent Document 10). Although high throughput sequence data suggest that RNA modification by substitution controls protein function by converting amino acid sequences, the detailed biological function of this RNA editing has not yet been revealed.

As described above, the detailed biological function of RNA editing has not yet been revealed; however, techniques for controlling site-specific RNA substitution editing remain an attractive tool to analyze and control biological processes related to RNA editing.

Ribozymes are meanwhile known as functional molecules which specifically recognize and react with a modified specific site in an RNA sequence. Among such ribozymes, a hammerhead ribozyme (HHR) which is the smallest RNA motif having catalytic action can cleave an RNA phosphodiester bond at a specific site, and the smallest hammerhead ribozyme (HHR) which cleaves a trans type is created by modifying a natural HHR (Non-Patent Document 11), and is used for suppressing in vivo target gene expression by gene control through RNA (Non-Patent Document 12). A HHR is composed of an active region having a conserved core sequence with catalytic activity at the central portion (Helix II), and recognition regions having two hybridizing arm sequences which recognize target sequences existing on the 3' side and 5' side of the active region (Helix III and Helix I, respectively).

A target-specific hammerhead ribozyme (HHR) can be produced by converting the hybridizing arm sequence corresponding to target RNA according to simple Watson-Crick base pairing rule. A HHR with variously different core sequences corresponding to target RNA can be designed and can be bound to target RNA by using a sequence complementary to a hybridizing sequence including a specific triplet of target RNA, and can cleave the phosphodiester bond existing on the 3' side of the triplet (Non-Patent Document 13).

Such hammerhead ribozyme (HHR) can in vitro and in vivo cleave mRNA in a mutation-specific manner (Non-Patent Document 14). These mutation-specific properties of HHR are produced based on the triplet to be preferentially cleaved. As described above, some HHRs which can cleave target RNA in a mutation-specific manner are created; however, a HHR which can specifically recognize RNA modification by substitution has not been reported.

PRIOR ART DOCUMENTS

Non-Patent Documents

Non-Patent Document 1: Maas, S. and Rich, A. 2000. Changing genetic information through RNA editing. Bioessays 22(9): 790-802; Bass, B. L. 2002. RNAediting by adenosine deaminases that act on RNA. Annu RevBiochem 71: 817-846; Farajollahi, S. and Maas, S. 2010. Molecular diversity through RNA editing: a balancing act. Trends Genet 26(5): 221-230; Nishikura, K. 2010. Functions and regulation of RNA editing by ADAR deaminases. Annu Rev Biochem 79: 321-349.

Non-Patent Document 2: Nishikura, K. 2010. Functions and regulation of RNA editing by ADAR deaminases. Annu RevBiochem 79: 321-349; Pullirsch, D. and Jantsch, M. F. 2010. Proteomediversification by adenosine to inosine RNA editing. RNA Biol 7(2): 205-212.

Non-Patent Document 3: Burns, C. M., Chu, H., Rueter, S. M., Hutchinson, L. K., Canton, H., Sanders-Bush, E., and Emeson, R. B. 1997. Regulation of serotonin-2C receptor G-protein coupling by RNA editing. Nature 387(6630): 303-308; Sommer, B., Kohler, M., Sprengel, R., and Seeburg, P. H. 1991. RNA editing in brain controls a determinant of ion flow in glutamate-gated channels. Cell 67(1): 11-19

Non-Patent Document 4: Werry, T. D., Loiacono, R., Sexton, P. M., and Christopoulos, A. 2008. RNA editing of theserotonin 5HT2C receptor and its effects on cell signalling, pharmacology and brain function. Pharmacol Ther 119(1): 7-23.

Non-Patent Document 5: Terada, S., et al., Fukuoka University science reports 40(1) 116-123 (2010)

Non-Patent Document 6: Higuchi, M., Single, F. N. Kohler, M., Sommer, B., Sprengel, R., and Seeburg, P. H. 1993. RNA editing of AMPA receptor subunit GluR-B: a base-paired intron-exon structure determines position and efficiency. Cell 75(7): 1361-1370.

Non-Patent Document 7: Blanc, V. and Davidson, N. O. 2003. C-to-U RNA editing: mechanisms leading to genetic diversity. J Biol Chem 278(3): 1395-1398.

Non-Patent Document 8: Wang, A. B., Liu, D. P., and Liang, C. C. 2003. Regulation of humanapolipoprotein B gene expression at multiple levels. Exp Cell Res 290(1):1-12.

Non-Patent Document 9: Maas, S., Kawahara, Y., Tamburro, K. M., and Nishikura, K. 2006. A-to-I RNA editing and human disease. RNA Biol 3(1): 1-9.

Non-Patent Document 10: Levanon, E. Y., Hallegger, M., Kinar, Y., Shemesh, R., Djinovic-Carugo, K., Rechavi, G, Jantsch, M. F., and Eisenberg, E. 2005. Evolutionarily conserved human targets of adenosineto inosine RNA editing. Nucleic Acids Res 33(4): 1162-1168; Gommans, W. M., Tatalias, N. E., Sie, C. P., Dupuis, D., Vendetti, N., Smith, L., Kaushal, R., and Maas, S. 2008. Screening of human SNP database identifies recoding sites of A-to-I RNA editing. RNA 14(10): 2074-2085; Li, J. B., Levanon, E. Y., Yoon, J. K., Aach, J., Xie, B., Leproust, E., Zhang, K., Gao, Y., and Church, G. M. 2009. Genome-wide identification of human RNA editing sites by parallel DNA capturing and sequencing. Science 324(5931): 1210-1213; Pullirsch, D. and Jantsch, M. F. 2010. Proteome diversification byadenosine to inosine RNA editing. RNA Biol 7(2): 205-212.

Non-Patent Document 11: Uhlenbeck, O. C. 1987. A small catalytic oligoribonucleotide. Nature 328(6131): 596-600; Haseloff, J. and Gerlach, W. L. 1988. Simple RNA enzymes with new and highly specific endoribonuclease activities. Nature 334(6183): 585-591.

Non-Patent Document 12: Goodchild, J. 2002. Hammerhead ribozymes for target validation. Expert Opin Ther Targets 6(2): 235-247; Citti, L. and Rainaldi, G 2005. Synthetic hammerhead ribozymesas therapeutic tools to control disease genes. Curr Gene Ther 5(1): 11-24; Tedeschi, L., Lande, C., Cecchettini, A., and Citti, L. 2009. Hammerhead ribozymes in therapeutic target discovery and validation. Drug Discov Today 14(15-16): 776-783.

Non-Patent Document 13: Kore, A. R., Vaish, N. K., Kutzke, U., and Eckstein, F. 1998. Sequence specificity of the hammerhead ribozyme revisited; the NHH rule. Nucleic Acids Res 26(18): 4116-4120

Non-Patent Document 14: Scherr, M., Grez, M., Ganser, A., and Engels, J. W. 1997. Specific hammerheadribozyme-mediated cleavage of mutant N-ras mRNA in vitro and ex vivo. Oligoribonucleotides as therapeutic agents. J Biol Chem 272(22): 14304-14313; Lewin, A. S., Drenser, K. A., Hauswirth, W. W., Nishikawa, S., Yasumura, D., Flannery, J. G., and LaVail, M. M. 1998. Ribozyme rescue of photoreceptor cells in a transgenic rat model of autosomal dominantretinitis pigmentosa. Nat Med 4(8): 967-971; Dawson, P. A. and Marini, J. C. 2000. Hammerhead ribozymes selectively suppress mutant type I collagen mRNA in osteogenesisimperfecta fibroblasts. Nucleic Acids Res 28(20): 4013-4020.

DISCLOSURE OF THE INVENTION

Problems to be Solved by the Invention

The present inventor, therefore, focused on a hammerhead ribozyme (HHR) which is an RNA molecule having catalytic action to cleave a phosphodiester bond at a specific site in RNA. As a result of intensive research on functionality which specifically recognizes and reacts with modification in RNA sequences, the present inventor found that a hammerhead ribozyme (HHR) acts as a functional molecule which specifically recognizes and reacts with the modification site of target RNA, thereby completing the present invention.

That is, the hammerhead ribozyme (HHR) according to the present invention was designed based on the target specificity of HHR to 3 bases (triplet) to be preferentially cleaved in target RNA so that it becomes possible to specifically cleave modification sites by RNA editing and the like.

For the creation of the hammerhead ribozyme (HHR) of the present invention, a HHR acting on a trans type was utilized as a tool to mutation-specifically cleave a target. The cleavage activity of HHR, however, is significantly affected by not only the triplet which is preferentially cleaved but also base pairing close to the core sequence of HHR having catalytic activity. Therefore, by utilizing this HHR base as a modification recognition base, a ribozyme specific to RNA modification was designed based on base pairing of the HHR base.

The hammerhead ribozyme (HHR) designed based on the theory can be represented by the constitutional formula in FIG. 3. In the constitutional formula in FIG. 3, the molecule in the upper row represented by the black thick solid line shows a hammerhead ribozyme. This hammerhead ribozyme (HHR) is composed of three regions, that is, an active region having a core sequence having catalytic activity at the central portion (Helix II), the 5' side recognition region which is located on the 5' side of the active region and has an arm sequence hybridizing with target RNA (substrate RNA) (Helix I) and the 3' side recognition region which is located on the 3' side thereof and has an arm sequence hybridizing with target RNA (substrate RNA) (Helix III). The 5' side recognition region (Helix I) and the 3' side recognition region (Helix III) each having an arm sequence are designed to hybridize with target RNA (substrate RNA).

Further, this hammerhead ribozyme (HHR) is designed so that the base (D) will exist in a position sandwiched between the 3' side recognition region (Helix III) and the active region (Helix II) and the base (X) will exist in a position sandwiched between the active region (Helix II) and the 5' side recognition region (Helix I). The base (D) forms a base pair with a target RNA base and by base-pairing with the base H of the triplet represented by 3'-NHH'-5' (the constitutional formula in FIG. 3) in target RNA, cleavage activity appears. The base (X) is meanwhile designed to form a base pair only with a modification site (editing site) of target RNA. Therefore, cytosine is used as a recognition base for A-to-I editing-specific cleavage. Similarly, for C-to-U editing-specific cleavage, guanosine is converted to adenosine and thus adenosine is used as a recognition base. As will be understood, when a base of target RNA is converted to another base by another modification other than A-to-I editing and C-to-U editing, it is needless to say that the recognition base of HHR can be designed to correspond to the converted base.

The molecule in the lower row, represented by the black solid line in the constitutional formula in FIG. 3, meanwhile shows target RNA (substrate RNA). This target RNA hybridizes with the 5' side recognition region (Helix I) and the 3' side recognition region (Helix III) of HHR to form each base pair. When the modification site (represented by "edit" herein) exists in the target RNA (substrate RNA), this modification site hybridizes with the recognition base of HHR to form a base pair and the bond of this modification site and the base adjacent to the 3' side of the modification site is cleaved. Here, the triplet represented by 3'-NHH'-5' in the constitutional formula in FIG. 3 shows a site with particularly high cleavage activity and is a site to be preferentially cleaved (Cleavage Site) by catalytic action of HHR. In the constitutional formula, N may be any nucleotide and H represents adenosine (A), cytosine (C) or uracil (U) (Kore et al. 1998).

Therefore, an object of the present invention is to provide a hammerhead ribozyme (HHR) for identifying RNA modification on target mRNA, for example, modification such as RNA editing (A-to-I editing and C-to-U editing etc.).

Another object of the present invention is to provide a hammerhead ribozyme target RNA structure which is a base-paired form between a hammerhead ribozyme (HHR) and target RNA.

Yet another object of the present invention is to provide a method for cleaving target RNA, the method including cleaving a specific modification site of target RNA by base pairing of a hammerhead ribozyme (HHR) and target RNA.

Solutions to the Problems

To achieve the objects, the present invention provides a hammerhead ribozyme which can recognize modified target RNA as described above, wherein the hammerhead ribozyme is represented by the general formula [I]:

[Chem. 1]

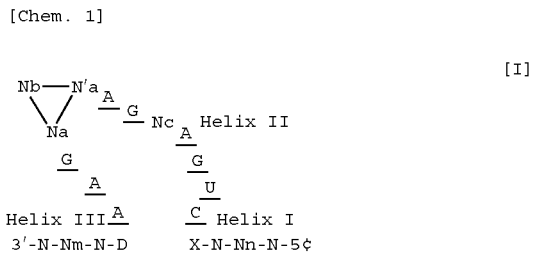

(wherein A means adenine (A);
C means cytosine (C);
G means guanine (G);
U means uracil (U);
D means adenine (A), cytosine (C), guanine (G) or uracil (U);
X is a modification recognition base which recognizes the modification site of target RNA, and means adenine (A), cytosine (C), guanine (G) or uracil (U);
N, all of which may be the same or different, means any base selected from adenine (A), cytosine (C), guanine (G) and uracil (U);
N', which may be the same or different, is any base selected from adenine (A), cytosine (C), guanine (G) and uracil (U), and means a base which forms a base pair with a corresponding base N;
a means an integer from 1 to 10, preferably an integer from 2 to 6, and more preferably an integer from 2 to 4;
b means an integer from 1 to 6, and preferably an integer from 2 to 4;
c means an integer from 1 to 4, and preferably an integer from 1 to 2;
m means an integer from 2 to 50, preferably an integer from 5 to 30, and further preferably an integer from 5 to 20; and
n means an integer from 2 to 50, preferably an integer from 5 to 30, and further preferably an integer from 5 to 20).

As a preferred embodiment of the present invention, there is provided a hammerhead ribozyme represented by the general formula [Ia]:

[Chem. 2]

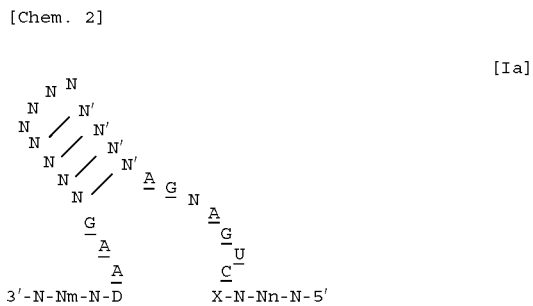

(wherein A, C, G, U, D, X, N and N' all have the same meaning as above).

As a further preferred embodiment of the present invention, there is provided a hammerhead ribozyme in which the base X is adenine (A) or cytosine (C) in the general formula [Ia].

Target RNA which the hammerhead ribozyme (HHR) of the present invention can recognize, meanwhile, can be represented by the general formula [II]:

[Chem. 3]

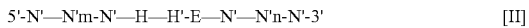

(wherein N' is any base selected from adenine (A), cytosine (C), guanine (G) and uracil (U), and means a base which forms a base pair with a corresponding base N in the hammerhead ribozyme (HHR);
H is any base selected from adenine (A), cytosine (C), guanine (G) and uracil (U), and means a base which forms a base pair with the corresponding base D in the HHR;
H' means any base selected from adenine (A), cytosine (C), guanine (G) and uracil (U);
E is any base selected from adenine (A), cytosine (C), guanine (G), uracil (U) and inosine (I) and is a base which forms a base pair with the corresponding base X in the HHR [I], and, when forming a base pair with the base X, means a base which cleaves the bond with the base H' adjacent to the 5' side; and
m and n both have the same meaning as above).

Therefore, the present invention provides a hammerhead ribozyme target RNA structure constructed by forming base pairs from the hammerhead ribozyme and the target RNA, wherein the hammerhead ribozyme target RNA structure is represented by the general formula [III]:

[Chem. 4]

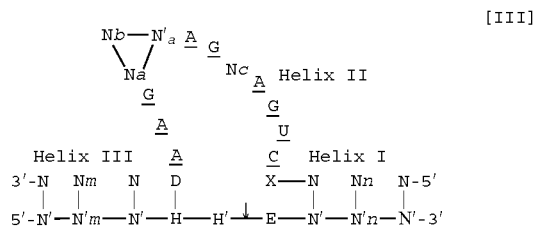

(wherein A, C, G, U, D, X, N, N', E, H, H', a, b, c, m and n all have the same meaning as above and the arrow shows the cleavage site).

The present invention provides, as another preferred embodiment thereof, a hammerhead ribozyme target RNA structure constructed by base pairing of the hammerhead ribozyme [Ia] and the target RNA [II], wherein the hammerhead ribozyme target RNA structure is represented by the general formula [IIIa]:

[Chem. 5]

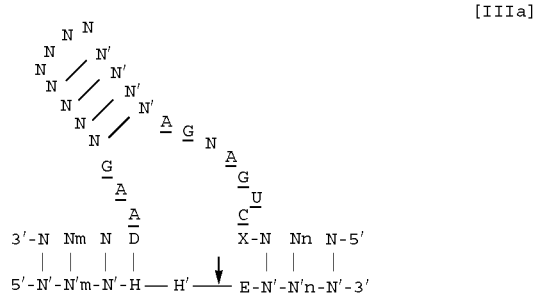

(wherein A, C, G, U, D, X, N, N', E, H, H', a, b, c, m and n all have the same meaning as above).

As a further preferred embodiment, the present invention provides a hammerhead ribozyme target RNA structure, wherein in the general formula [IIIa], when the base E is the base I, the base X is the base C, and when the base E is the base U, the base X is the base A.

As another further preferred embodiment, the present invention provides a hammerhead ribozyme target RNA structure, wherein in the general formula [IIIa], when the base E is the base I, the base X is the base C, and when the base E is the base U, the base X is the base A.

Further, the present invention provides a method for cleaving RNA modification using the HHR, the method including cleaving the cleavage site of the target RNA portion of the structure. More specifically, the present invention provides a method for cleaving RNA using the HHR, the method including cleaving the binding site adjacent to the upstream 5' side of the modification site existing on target RNA.

The hammerhead ribozyme (HHR) according to the present invention has high cleavage activity to the triplet sequence 5'-N'HH'-3' (wherein, preferably the base N' is adenine (A), uracil (U), guanine (G) or cytosine (C) and the base H and the base H' are A, C or U) which is a surrounding sequence of the cleavage site of target RNA. Both the base H and the base H' do not represent guanine (G), and it is believed that when the base H and the base H' are guanine (G), the cleavage activity hardly exists. When the cleavage activity is generated, however, the base H and the base H' may be guanine (G). It is reported that when the triplet sequence is NUC, the cleavage activity is high, and thus this triplet sequence is also naturally encompassed in the scope of the present invention.

BRIEF DESCRIPTION OF THE DRAWINGS

FIG. 7 shows graphs showing the analytical results of cleaved bands by Image J.

FIG. 12 is an electropherogram showing the cycle check results of Round 8.

FIG. 13 is a diagram showing sequence analysis results of Library H1.

FIG. 14 is a diagram showing sequence analysis results of Library H2.

FIG. 15 is a diagram showing sequence analysis results of Library H2 for a second time.

FIG. 18(A) is a diagram showing the base sequences of the ribozyme and the HTR2C RNA fragment. FIG. 18(B) is a diagram showing the analytical results of A-to-I editing-specific cleavage by ribozymes using denatured PAGE (15%). FIG. 18(C) is a graph summarizing the cleavage ratio obtained by the experiments of HR-HTR2C and HR-HTR2C-edit to HTR2C-ade and HTR2C-ino.

FIG. 19 shows the results of cleavage reactions over time and kinetic analysis of HR-HTR2C and HR-HTR2C-edit to edited and unedited HTR2C RNA fragments under single turnover conditions.

FIG. 20 shows C-to-U editing-specific cleavage of a ribozyme to an APOB mRNA fragment. FIG. 20(A) is a diagram showing the base sequences of the ribozyme and the APOB mRNA fragment. FIG. 20(B) is a diagram showing the analytical results of C-to-U editing-specific cleavage of a ribozyme, HR-APOB-edit, using denatured PAGE (15%). FIG. 20(C) is a graph showing the results of cleavage reactions over time and kinetic analysis of HR-APOB-edit to unedited and edited APOB RNA fragments.

FIG. 21 shows denatured PAGE (15%) showing cleavage over time of HR-APOB-edit to HR-APOB-ade (upper row) and HR-APOB-ino (lower row).

FIG. 22 shows A-to-I editing-specific cleavage to FLNA mRNA. FIG. 22(A) is a diagram showing the base sequences of a ribozyme and a synthetic FLNA mRNA fragment. FIG. 22(B) is a diagram showing the analytical results of A-to-I editing-specific cleavage by the ribozyme using denatured PAGE (15%). FIG. 22(C) is a graph summarizing the cleavage ratio obtained by experiments (B) of HR-FLNA and HR-FLNA-edit to FLNA-ade and FLNA-ino.

FIG. 23A is a drawing showing in vitro A-to-I editing-specific cleavage of a ribozyme to FLNA mRNA extracted from cells (a drawing showing an experimental technique for the editing-specific cleavage analysis of HR-FLNA-edit to FLNA mRNA extracted from cells by measuring editing ratios at the Q/R site).

BEST MODE FOR CARRYING OUT THE INVENTION

Figure 1:
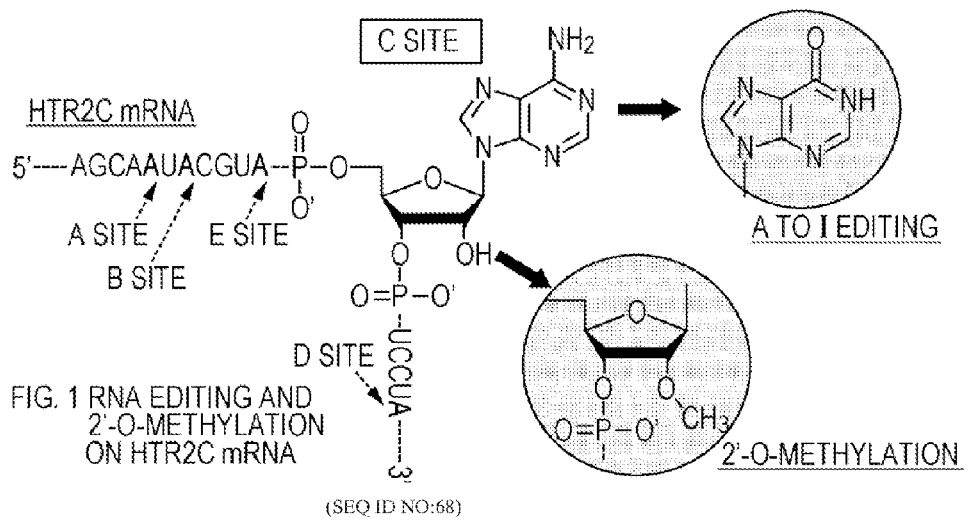
FIG. 1 is a drawing showing a site subjected to RNA editing (A-to-I editing) on serotonin 2C receptor (HTR2C).
Figure 2:
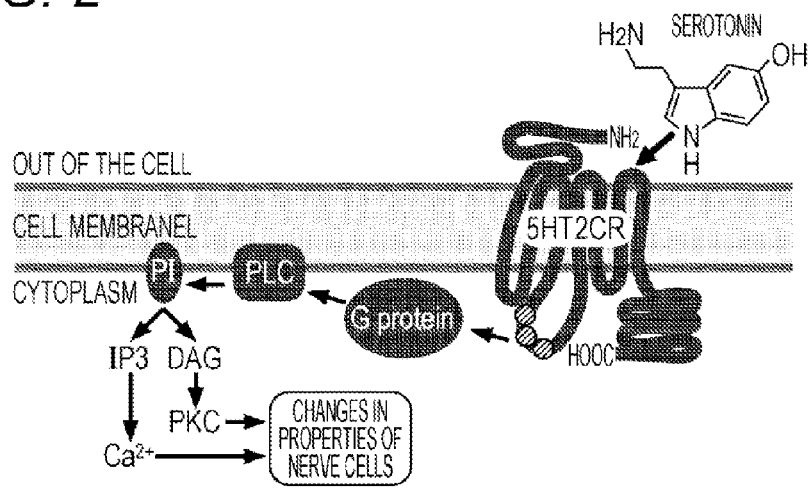
FIG. 2 is a drawing for explaining (A) the physiological functions of serotonin 2C receptor and (B) RNA editing thereof.
Figure 3:
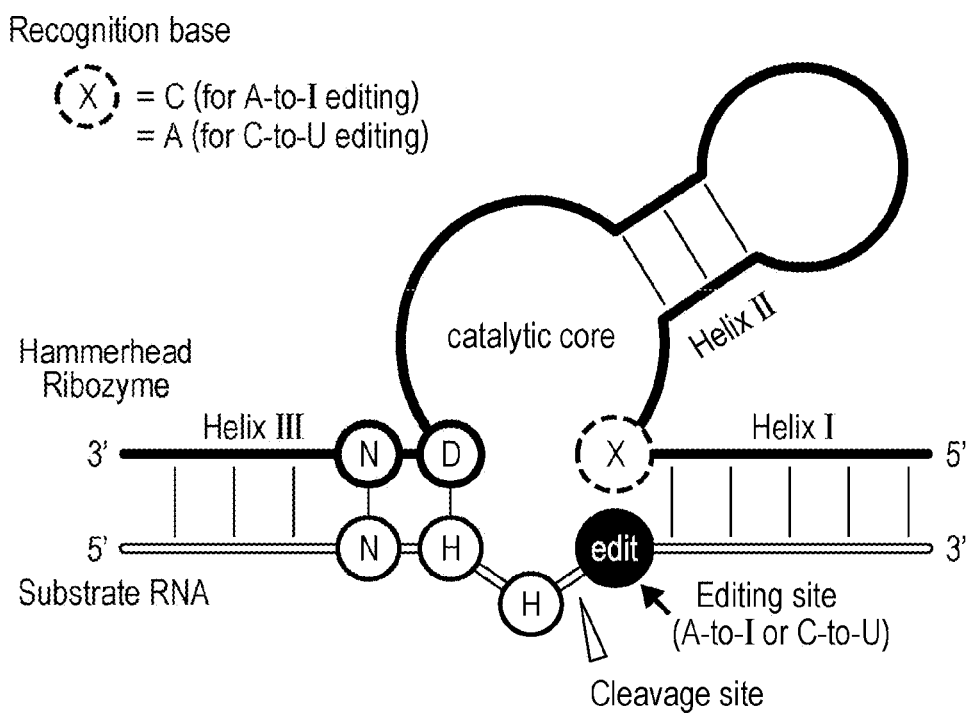
FIG. 3 is a schematic diagram showing the constitution of the hammerhead ribozyme (HHR) of the present invention.

The hammerhead ribozyme according to the present invention can be represented by the general formula [I]:

[Chem. 6]

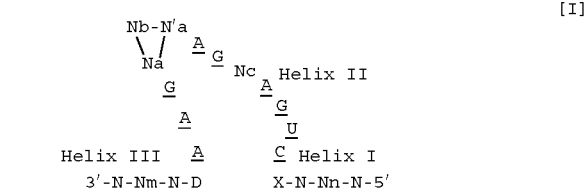

[I]

(wherein A means adenine (A);
C means cytosine (C);
G means guanine (G);
U means uracil (U);
D means adenine (A), cytosine (C), guanine (G) or uracil (U);
X is a modification recognition base which recognizes the modification site of target RNA, and means any base selected from adenine (A), cytosine (C), guanine (G) and uracil (U);
N, all of which may be the same or different, means any base selected from adenine (A), cytosine (C), guanine (G) and uracil (U);
N', which may be the same or different, is any base selected from adenine (A), cytosine (C), guanine (G) and uracil (U), and means a base which forms a base pair with a corresponding base N;
a means an integer from 1 to 10, preferably an integer from 2 to 6, and more preferably an integer from 2 to 4;
b means an integer from 1 to 6, and preferably an integer from 2 to 4;
c means an integer from 1 to 4, and preferably an integer from 1 to 2;
m means an integer from 2 to 50, preferably an integer from 5 to 30, and further preferably an integer from 5 to 20; and
n means an integer from 2 to 50, preferably an integer from 5 to 30, and further preferably an integer from 5 to 20).

The active region (Helix II) having the core sequence of the hammerhead ribozyme of the present invention is a region having the action of catalyzing cleavage activity at the modification site in modified target RNA, and can also be represented by the general formula [IV]:

[IV]

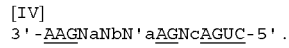

In the general formula [IV], underlined bases (A, C, G and U) show a base sequence (consensus sequence) causing the action of cleavage catalytic activity required for cleaving the modification site of target RNA.

The hammerhead ribozyme as a preferred embodiment of the present invention can be represented by the general formula [Ia]:

[Chem. 7]

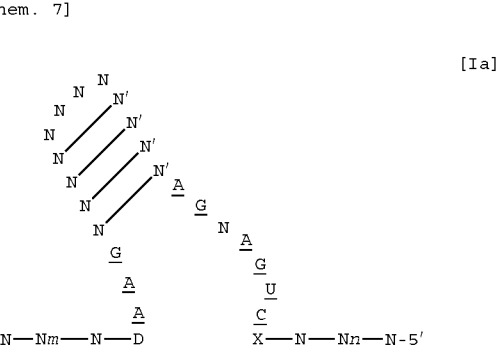

[Ia]

(wherein A, C, G, U, D, X, N and N' all have the same meaning as above).

Examples of target RNA recognized by the hammerhead ribozyme of the present invention include RNA precursors such as serotonin 2C receptor (HTR2C), glutamate receptor, γ-amino butyric acid (GABA) receptor, FLNA (filamin A, alpha [actin binding protein 280]), apolipoprotein B (ApoB), a receptor deeply involved in the neuropsychiatric function of the central nervous system such as potassium channels, and ion channels.

These target RNAs can be represented by the general formula [II]:

[Chem. 8]

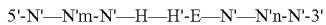

[II]

(wherein N', all of which may be the same or different, is any base selected from adenine (A), cytosine (C), guanine (G) and uracil (U), and means a base which forms a base pair with a corresponding base N in the hammerhead ribozyme (HHR); H is any base selected from adenine (A), cytosine (C), guanine (G) and uracil (U), and means a base which forms a base pair with the corresponding base D in the HHR [I]; H' means any base selected from adenine (A), cytosine (C), guanine (G) and uracil (U); E is any base selected from adenine (A), cytosine (C), guanine (G), uracil (U) and inosine (I), and is a base which forms a base pair with the corresponding base X in the HHR, and, when forming a base pair with the base X, means a base which cleaves the bond with the base H' adjacent to the upstream 5' side; and m and n both have the same meaning as above).

In target RNA, the base E means a base subjected to modification such as RNA editing and mutation and, for example when being subjected to A-to-I editing, means inosine (I), and when being subjected to C-to-U editing, means uracil (U). Therefore, the modification recognition base (X) of a hammerhead ribozyme which forms a base pair with target RNA [II] is preferably, when the base E of target RNA [II] is inosine (I), cytosine (C), and, when the base E of target RNA [II] is uracil (U), adenine (A).

Further, a three base sequence (triplet sequence) represented by the general formula 5'-N'HH'-3' is a surrounding sequence of the cleavage site of target RNA and is a base sequence sandwiched between the 3'-side region and the 5'-side region of target RNA, and shows high cleavage activity to the cleavage site of target RNA. That is, the hammerhead ribozyme (HHR) of the present invention shows high cleavage activity to the triplet sequence 5'-N'HH'-3' (wherein preferably the base N' is adenine (A), uracil (U), guanine (G) or cytosine (C), and the base H and the base H' are A, C or U). Both the base H and the base H' do not represent guanine (G), and it is believed that when the base H and the base H' are guanine (G), the cleavage activity does not exist or the cleavage activity hardly exists. When the cleavage activity can be generated by guanine (G), however, the base H and the base H' both may be guanine (G). It is reported that when the triplet sequence is NUC, the cleavage activity is high, and thus this triplet sequence is also naturally encompassed in the scope of the present invention.

That is, when target RNA [II] is subjected to modification such as RNA editing and mutation, the base at the site is converted to a base different from the original base. Consequently, the modified base forms a base pair with the modification recognition base of a ribozyme, and therefore, the binding site of the modified base and the base adjacent to the upstream 5' side thereof is cleaved.

Therefore, the present invention provides a hammerhead ribozyme target RNA structure obtained by reacting the hammerhead ribozyme with target RNA to form base pairs, wherein the hammerhead ribozyme target RNA structure is represented by the general formula [III]:

[Chem. 9]

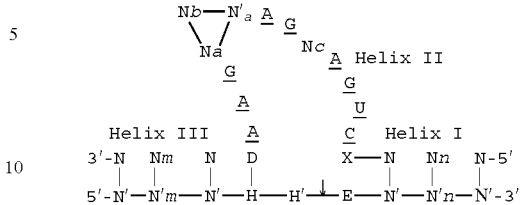

[III]

(wherein A, C, G, U, D, X, N, N', E, H, H', a, b, c, m and n all have the same meaning as above, and the arrow shows the cleavage site).

In the hammerhead ribozyme target RNA structure, the modification recognition base (X) of HHR cleaves the bond with the base (H') adjacent to the upstream 5' side of the modification site (E) by forming a base pair with the modification site (E) of target RNA. That is, the base (E) of target RNA, for example, means inosine (I) for A-to-I editing and means uracil (U) for C-to-U editing. Therefore, the modification recognition base (X) of a hammerhead ribozyme corresponding to the modified base (E) is cytosine (C) for A-to-I editing, and is adenine (A) for C-to-U editing.

The present invention provides, as a preferred embodiment thereof, a hammerhead ribozyme target RNA structure represented by the general formula [IIIa]:

[Chem. 10]

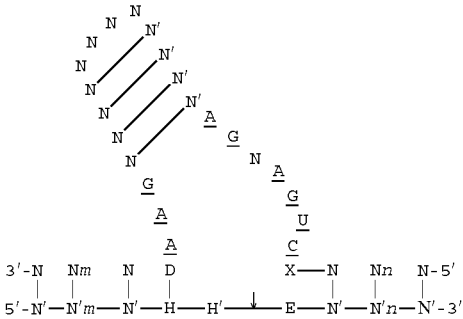

[IIIa]

(wherein A, C, G, U, D, X, N, N', E, H, H', a, b, c, m and n all have the same meaning as above).

As described above, the hammerhead ribozyme of the present invention recognizes the modification site of target RNA modified by, for example, RNA editing and the like and, when the modification recognition base (X) of the hammerhead ribozyme and the modified base (E) of target RNA form a base pair to construct a hammerhead ribozyme target RNA structure, the phosphodiester bond with the base (H') adjacent to the upstream 5' side of the modified base (E) of target RNA will be cleaved.

Consequently, target mRNA modified by RNA editing and the like will create a protein having functions and actions different from those from an original protein induced from target mRNA which is not subjected to such modification. Consequently, the hammerhead ribozyme of the present invention can suppress the functions and actions of modified target mRNA which has a possibility of having a bad influence on vital functions by reason that target mRNA is modified. Therefore, the hammerhead ribozyme of the present invention, for example, can be expected to be of help in the prevention and improvement in treatment of disorders such as mental disorders such as schizophrenia, bipolar disorder and major depressive disorder related to serotonin 2C receptor (HTR2C), glutamate receptor, γ-amino butyric acid (GABA) receptor, FLNA (actin binding protein 280), apolipoprotein B (ApoB), a receptor deeply involved in the neuropsychiatric function of the central nervous system such as potassium channels, and ion channels.

As shown in FIG. 1, for example, it is known that RNA editing occurs at the following sites among the 5 sites from the A to E sites in serotonin 2C receptor (HTR2C) RNA in a living body. As diseases related to such RNA editing, there are mentioned diseases as shown in Table 1 given below. Therefore, along with the above diseases, the hammerhead ribozyme according to the present invention can also be expected to be effective in diseases as shown in Table 1 given below.

TABLE 1

| Types of diseases | Development site of RNA editing |
|---|---|
| Depression, Schizophrenia | ↑ D |
| Schizophrenia | ↓ B |
| Depression | ↑ D |
| Suicide | ↑ A |
| Suicide, Mood disorder | ↑ CE, ↓ D |

In addition to these, RNA editing in regions encoding proteins is also known, and the hammerhead ribozyme [I] according to the present invention can be expected to be effective in diseases related to those genes and diseases as shown in Table 2 given below.

TABLE 2

| Name of Gene | Amino Acid (Codon) Before Editing | Amino Acid (Codon) After Editing | Gene-Associated Diseases |
|---|---|---|---|
| HMNC1 (hemicentin 1) | K(AAG) | E(IAG) | Age-related macular degeneration |
| BIN1 (bridging integrator 1) | K(AGG) | R(AIG) | Carcinogenesis |
| FLNB (filamin B, beta) | Q(CAG) | R(CIG) | Osteogenesis imperfection |
| ATXN (Ataxin-7) | K(AAA) | R(AIA) | Spinocerebellar degeneration type 7 |
| CCN I (cyclin I) | R(AAG) | G(UGG) | Pancreatic cancer |
| PTPRN2 (prtein tyrosine phosphatase, receptor type.N polypeptide 2) | E(CAG) | G(GIG) | Diabetes mellitus |
| PTK2 (protein tyrosine kinase 2) | T(ACG) | A(ICG) | Carcinogenesis |
| RSU1 (ras supressor protein 1) | M(AUG) | V(IUG) | Glioma |
| KIF20B (kinesin family member 20B) | K(AAG) | R(AIG) | Alzheimer's disease |
| CD6 (CD6 molecule) | S(AGC) | G(IGC) | Multiple sclerosis |
| GANAB (glucosidase, alpha:neutral AB) | Q(CAG) | R(CIG) | Male sterility |
| NUMA 1 (nuclear mitotic apparatus protein 1) | T(ACC) | A(ICC) | Breast cancer |
| OS9 (osteosacroma amplified 9) | E(GAG) | G(GIG) | Osteosarcoma |
| NEIL1 (nei endonuclease VIII-like 1) | K(AAA) | R(AIA) | Primary sclerosing cholangitis |
| SPSB3 (spIA/ryanodine receptor domain and SOCS box 3) | K(AAG) | R(AIG) | Schizophrenia, Autism |
| SS18L1 (SS18-like protein 1) | S(AGC) | G(IGC) | Synovial sarcoma |
| TRO (trophinin) | S(AUG) | G(IGU) | Ovarian cancer, Gallbladder cancer |

An example of a structure of a hammerhead ribozyme and serotonin 2C receptor (HTR2C) mRNA (HTR2C RNA) will be specifically described. It should be noted, however, that the present invention is not restricted to the HHR-HTR2C RNA structure. The constitution of the HHR-HTR2C RNA structure used in the present invention can be described as follows:

[Chem. 11]

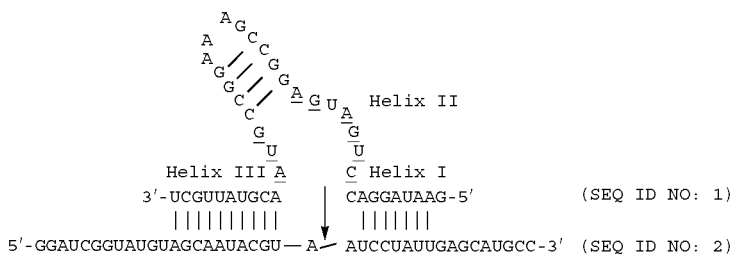

[IIIb]

(SEQ ID NO: 1)
(SEQ ID NO: 2)

(wherein underlined bases mean a consensus sequence required for catalytic activity).

In the constitutional formula [IIIb], the modification site (E) of HTR2C RNA is represented as adenosine (A), i.e. an unmodified site, and thus cannot form a base pair with cytosine (C) of the modification recognition base (X) of the hammerhead ribozyme. In the structure represented by the constitutional formula, therefore, cleavage will not occur at the cleavage site of HTR2C RNA. On the other hand, when the modification site (E) of HTR2C RNA is edited to inosine (I) by A-to-I editing, the base forms a base pair with the editing recognition site (C) and cleavage at the cleavage site shown by the arrow occurs.

In addition to the HTR2C RNA, examples of hammerhead ribozyme (HHR) RNA structures include a structure of HHR and FLNA (actin binding protein 280), a structure of HHR and ApoB (apolipoprotein B) and the like.

Here, the constitutional formula of the structure of HHR and FLNA (HHRz FLNA01) is as shown below.

[Chem. 12]

[IIIc]

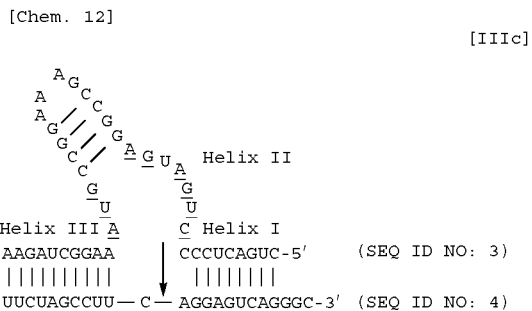

In addition, the constitutional formula [IIId] of the structure of HHR and ApoB (HHRz ApoB01) is as shown below.

[Chem. 13]

[IIId]

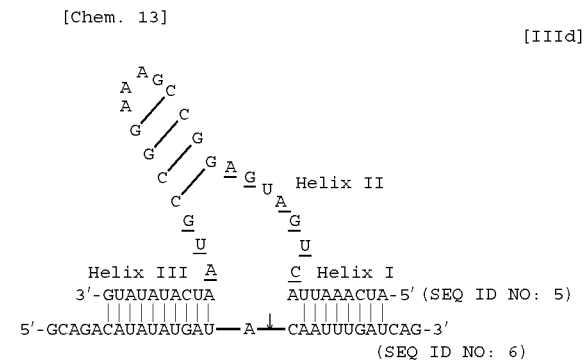

The hammerhead ribozyme (HHR) according to the present invention can be delivered to target cells by direct addition, forming a complex with a cationic lipid, wrapping in liposome or other forms. The hammerhead ribozyme of the present invention or a complex thereof can be topically administered to a related tissue ex vivo with or without incorporation into a biopolymer, or in vivo by injection, a pouring pump or a stent. Alternatively, the HHR of the present invention can be expressed by DNA vectors and RNA vectors delivered to cells and thus can also be expressed in cells from either an inducible or endogenous promoter. These recombinant vectors are preferably DNA plasmids, adenoviruses, retroviruses or adeno-associated virus vectors. Other mammalian cell vectors which direct the expression of RNA can also be used for this purpose. Such recombinant vectors can be topically delivered as described above, and delivered HHR cleaves target mRNA immediately after expression.

Normally, it is preferred that the composition of the liposome be steroid, particularly a combined substance with phospholipid combined with cholesterol, particularly a combined substance with phospholipid with high phase transition temperature. The physical properties of liposomes depend on pH, ion strength and the existence of divalent cations. The structure of the present invention can also be delivered as the expression vector of naked genes. This means that the structure of the present invention is not bound to delivery carriers (e.g. liposomes or colloidal particles). One of the main advantages expected in a naked vector is that there is not an immune response stimulated by the vector itself.

The present invention can be applied to gene therapy for treating diseases. Such therapy methods can display therapeutic effects by introducing a proper ribozyme which specifically cleaves mRNA into target cells with the disorders. Ribozymes can be delivered by using recombinant expression vectors like chimeric viruses or a colloidal dispersion system.

The gene therapy by the present invention can be carried out in vivo or ex vivo according to conventional methods. Examples of virus vectors which can be used include RNA viruses such as adenoviruses, herpes viruses, vaccinia and retroviruses. The retrovirus vectors are, for example, those derived from murine or avian retroviruses. Examples of retrovirus vectors into which a single foreign gene can be inserted include, for example, Moloney murine leukemia virus (MoMuLV), Harvey murine sarcoma virus (HaMuSV), mouse mammary tumor virus (MuMTV) and Rous sarcoma virus (RSV).

The present invention will be now described in more detail by way of examples thereof. It should be understood, however, that the following examples are described only for the purpose of explaining the present invention in more detail and are not intended to limit the present invention at all. Therefore, it should be understood that various variations considered based on the following examples are encompassed in the scope of the present invention.

EXAMPLE 1

Figure 18:
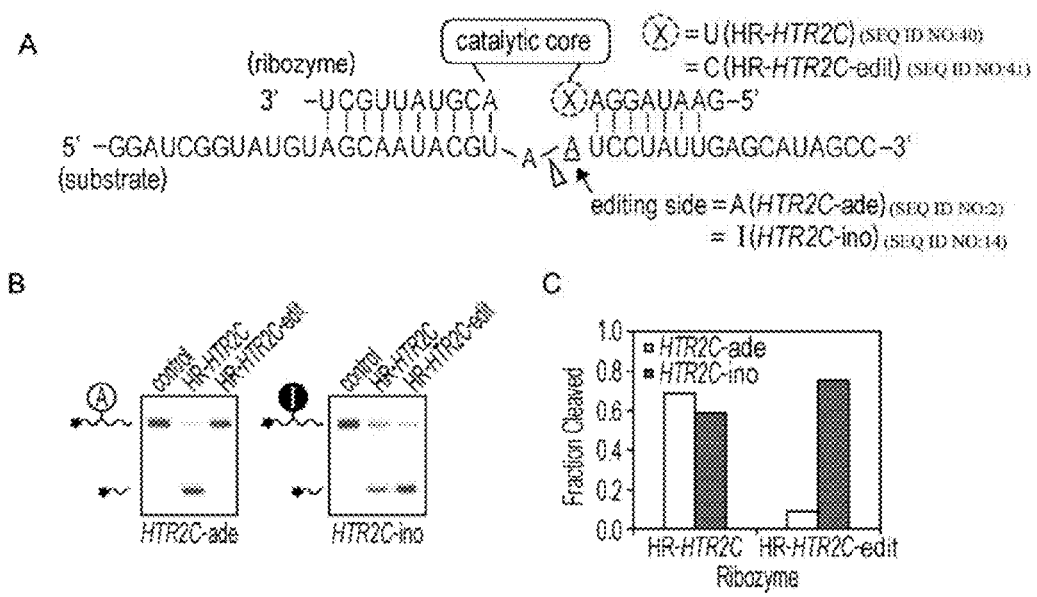
FIG. 18 shows A-to-I editing-specific cleavage of a ribozyme corresponding to a HTR2C RNA fragment.

In the present example, the A-to-I editing site on HTR2C mRNA, i.e. the C site, was selected as a target modification site to evaluate the effectiveness of editing-specific cleavage of a designed ribozyme. In addition, in order to construct a ribozyme having the activity of A-to-I editing-specific cleavage, HHR (HR-HTR2C) was designed according to a common method to contain a core sequence having catalytic activity and 16 bases complementary to HTR2C RNA for cleaving C at the 5' position (FIG. 18A).

The core sequence (Helix II) having catalytic activity used in the present example is as shown below.

(SEQ ID NO: 7)
5'-CUGANcGAGGCC GAAAGGCCGAA-3'

This sequence is composed of a consensus sequence (5'-CUGANGA----GAA-3') and a 4 base pair (bp) GCGC duplex and a stem loop structure containing a GAAA tetraloop (Scott, W. G., et al. 1995. Cell 81(7): 991-1002). Since the front and back of the target cleavage site sequence (GUA triplet) in the constitution is selected based on the triplet rule, HHR is expected to show cleavage activity to HTR2C RNA. In the obtained HHR structure, therefore, the modification recognition base forms a U-A base pair (A is the modification site) at the C site. An editing-specific ribozyme is constructed by converting the recognition base U to C to show the cleavage activity only when A at the C site is substituted by I by A-to-I RNA editing (FIG. 18A). Inosine forms a base pair with cytosine which is the same as in a G-C base pair. Consequently, a ribozyme to be obtained acquires the ability to identify the modification site of target RNA by base pair recognition. Therefore, the cleavage ability of this ribozyme to edited HTR2C (HR-HTR2C-edit) is expected to be higher than that to unedited HTR2C.

The sequences of oligonucleotide obtained in the following examples are as described in Table 3 given below.

TABLE 3

| Designation | Sequences of oligonucleotide and deoxyoligonucleotide (5'→3') |
|---|---|
| HR-HTR2C | AGCAATACGTTTCGGCCTTTCGGCCTCATCAGATCCTATTCTATAGTGAGTCGTATTAG (SEQ ID NO: 8) |
| HR-HTR2C-edit | AGCAATACGTTTCGGCCTTTCGGCCTCATCAGGTCCTATTCTATAGTGAGTCGTATTAG (SEQ ID NO: 9) |
| HR-APOB-edit_F | CTAATACGACTCACTATAGGGATCAAATTAC (SEQ ID NO: 10) |
| HR-APOB-edit_R | CATATATGATTTCGGCCTTTCGGCCTCATCAGTAATTTGATCCCTATAG (SEQ ID NO: 11) |
| HR-FLNA-edit_F | CTAATACGACTCACTATAGGGCTGACTCC (SEQ ID NO: 12) |
| HR-FLNA-edit_R | TTCTAGCCTTTTCGGCCTTTCGGCCTCATCAGGGGAGTCAGCCCTATAG (SEQ ID NO: 13) |
| HTR2C-ino | GGAUCGGUAUGUAGCAAUACGUA1UCCUAUUGAGCAUAGCC (SEQ ID NO: 14) |
| APOB-uri | GCAGACAUAUAUGAUAUAAUUUGAUCAG (SEQ ID NO: 15) |
| APOB-cyi | GCAGACAUAUAUGAUACAAUUUGAUCAG (SEQ ID NO: 16) |
| FLNA-ade | UUCUAGCCUUCAGGAGUCAGGGC (SEQ ID NO: 4) |
| FLNA-ino | UUCUAGCCUUC1GGAGUCAGGGC (SEQ ID NO: 17) |

The materials, reagents and the like used in the present example are as shown below.
(In vitro transcription reagents)
RNase-Free water, 10× AmpliScribe T7 Reaction Buffer, 25 mM NTP, 100 mM DTT,
RiboGuard RNase Inhitor, AmpliScribe T7 or Enzyme Solution: AmpliScribe
(PCR Reagents)
Taq DNA Polymerase, 10× Thermo Pol Reaction Buffer: NEB
2.5 mM dNTP, 2 mM dNTP:
(Reverse transcription reagents)
AMV Reverse Transcriptase 10 U/μl, AMV RT 5× BUFFER, 10 mM dNTP: Promega
(Dephosphorylating reagents)
Antarctic Phasshatase 5000 U/ml, 10× Antarctic Phasphatase buffer: NEB
(Phosphorylating reagents)
T4 Polynucleotide kinase, 10×T4 Polynucleotide Kinase Buffer: TAKARA
NEG 502Z [gamma-$^{32}$P] 222 TBq/mmol (6000 Ci/mmol) 370 MBq/ml: PerkinElmer
(Restriction enzymes)
BamH I 10 U/μl: TOYOBO
EcoR I 70 U/μl: Promega 10× H buffer: TAKARA
(Other)
2× Ligation mix
Oligo DNAs were acquired from Genenet, co., ltd. by a conventional method.

HRz1C (53 nt)
(SEQ ID NO: 18)
5'-GCAATACGTATTCGAAAACTCATCAGTCCTATTGCTATAGTGAGTCGTATTAG-3'

HRz 2C (59 nt)
(SEQ ID NO: 19)
5'-GCAATACGTATTCGGCCTTTCGGCCTCATCAGTCCTATTGCTATAGTGAGTCGTATTAG-3'

HRzC 1E (53 nt)
(SEQ ID NO: 20)
5'-AGCAATACGTTTCGAAAACTCATCAGATCCTATTCTATAGTGAGTCGTATTAG-3'

HRzC 2E (59 nt)
(SEQ ID NO: 21)
5'-AGCAATACGTTTCGGCCTTTCGGCCTCATCAGATCCTATTCTATAGTGAGTCGTATTAG-3'

S (40 nt)
(SEQ ID NO: 22)
5'-CAATAGGATTACGTATTGCTACTATAGTGAGTCGTATTAG-3'

S5 (59 nt)
(SEQ ID NO: 23)
5'-GGCTATGCTAATAGGATTACGTATTGCTACATACCGATCCTATAGTGAGTCGTATTAG-3'

T7proG cap
(SEQ ID NO: 24)
5'-CTAATACGACTCACTATAG-3'

(Library H (+)) (29 mer)
(SEQ ID NO: 25)
5'-CTAATACGACTCACTATAGGCTATGCTCA-3'

(Library H1 (-)) (59 mer)
(SEQ ID NO: 26)
5'-GGTATGTAGCAATACGTA (N24)TCCTATTGAGCATAGCC-3'

(Library H2 (-)) (63 mer)
(SEQ ID NO: 27)
5'-GGTATGTAGCAATACGTA (N24)TCCTAT (N4)TGAGCATAGCC-3'

HRzC-ino (59 nt)
(SEQ ID NO: 8)
5'-AGCAATACGTTTCGGCCTTTCGGCCTCATCAGGTCCTATTCTATAGTGAGTCGTATTAG-3'

Primers
(Library H (+)) (29 mer)
(SEQ ID NO: 28)
5'-CTAATACGACTCACTATAGGCTATGCTCA-3'

Selection H RT16 nt
(SEQ ID NO: 29)
5'-GGTATGTAGCAATACG-3'

HHSeq_F_EcoRI (26 mer)
(SEQ ID NO: 30)
5'-CGGAATTCTAATACGACTCACTATAG-3'

-continued

HHSeq_R_BamHI (25 mer)
(SEQ ID NO: 31)
5'-GCGGGATCCGGTATGTAGCAATACG-3'

Modified RNAs were acquired from Hokkaido System
Science Co., Ltd.
5'-end biotinylated S (27 nt)
(SEQ ID NO: 32)
5'-CAUUACGUAAUCCUAUUGAGCAUAGCC-3'

S C-ino (41 nt)
(SEQ ID NO: 14)
5'-GGAUCGGUAUGUAGCAAUACGUAIUCCUAUUGAGCAUAGCC-3'

EXAMPLE 2

As a design for ribozymes (HRz1E and HRz2E) which cleave the E site on HTR2C mRNA (control), the E site-cleaving ribozymes (HRz1E and HRz2E) in which the cleavage sites of HRz1C and HRz2C are shifted to the 5' side by a base were designed so that a surrounding sequence of the cleavage site would accord with the 5'—Nn'HH'-3' rule (triplet rule).

The specific sequences of the E site-cleaving ribozymes (HRz1E and HRz2E) are as shown in the following formulae (1) to (2).

HRz1E (35 nt):
[Chem. 14]
(1)
(SEQ ID NO: 33)
5'-G[AAUAGGAU]CUGAUGAGUUUUCGAA[ACGUAUUGCU]-3'

HRz2E (41 nt):
[Chem. 15]
(2)
(SEQ ID NO: 34)
5'-G[AAUAGGAU]CUGAUGAGGCCGAAAGGCCGAA[ACGUAUUGCU]-3'

Next, ribozymes (HRz1C, HRz2C, HRz1E and HRz2E) and substrate RNAs (S1, S2, S3, S4 and S5) (target sequences) were synthesized as follows.

As a design for ribozymes (HRz1C and HRz2C), the target recognition region was converted to a sequence complementary to the sequence of HTR2C mRNA so that the C site on HTR2C mRNA would be a cleavage site. Since it has been already reported that the number of stems existing in the active region has an effect on cleavage activity, a ribozyme with a stem (HRz1C: 35 nt) and a ribozyme with 4 stems (HRz2C: 41 nt) were designed. In these two types of ribozymes, however, a surrounding sequence of the cleavage site is (5'-UAA-3'), and the sequence is not applied to the 5'-N'HH'-3' rule (triplet rule), and thus the activity is expected to be low.

The specific sequences of the ribozymes (HRz1C and HRz2C) are as shown in the following formulae (3) to (4).

HRz1C (35 nt):
[Chem. 16]
(3)
(SEQ ID NO: 35)
5'-G[CAAUAGGA]CUGAUGAGUUUUCGAA[UACGUAUUGC]-3'

HRz2C (41 nt):
[Chem. 17]
(4)
(SEQ ID NO: 36)
5'-G[CAAUAGGA]CUGAUGAGGCCGAAAGGCCGAA[UACGUAUUGC]-3'

In the sequences, the base group in the left box shows Helix I (5'-recognition region), the underlined base group shows a stem region, and the base group in the right box shows Helix III (3'-recognition region). The same applies to the rest.

Ribozymes (HRz1E and HRz2E) can also be designed and synthesized in substantially the same manner as for ribozymes (HRz1C and HRz2C).

First, in order to add T7 promoter to the upstream sequence of each ribozyme, annealing was carried out using the following composition by heating at 98° C. for 5 minutes and then gradually cooling to 25° C. over an hour.

TABLE 4

Table: Composition to add T7 promoter to HRz1C

| Material | Quantity |
| --- | --- |
| 10× annealing buffer (50 mM Tris-HCl [pH 7.6], 50 mM NaCl) | 2 µl |
| T7 promoter | 10 µl |
| HRz1C oligo DNA | 8 µl |

TABLE 5

Table: Composition to add T7 promoter to HRz2C

| Material | Quantity |
| --- | --- |
| 10× annealing buffer | 2 µl |
| T7 promoter | 10 µl |
| HRz2C oligo DNA | 8 µl |

TABLE 6

Table: Composition to add T7 promoter to HRz3C

| Material | Quantity |
| --- | --- |
| 10× annealing buffer | 2 µl |
| T7 promoter | 10 µl |
| HRz3C oligo DNA | 8 µl |

TABLE 7

Table: Composition to add T7 promoter to HRz4C

| Material | Quantity |
| --- | --- |
| 10× annealing buffer | 2 µl |
| T7 promoter | 10 µl |
| HRz4C oligo DNA | 8 µl |

TABLE 8

Table: Composition to add T7 promoter to substrate S (target sequence)

| Material | Quantity |
| --- | --- |
| 10× annealing buffer | 2 µl |
| T7 promoter | 10 µl |
| S oligo DNA | 8 µl |

Using a sample after annealing as a template, RNA (ribozyme) was synthesized by an in vitro transcription reaction (37° C.: 3 hours) in a solution with the following composition.

TABLE 9

Table: Composition of reaction solution to synthesize RNA (ribozyme) sample

| Material | Quantity |
|---|---|
| RNase-Free Water | 13.5 μl |
| Template DNA | 1.5 μl (1 μg) |
| 10× AmpliScribe T7 Reaction Buffer | 4 μl |
| 2.5 mM NTP | 12 μl |
| 100 mM DTP | 4 μl |
| RiboGuard RNase Inhibitor | 1 μl |
| AmpliScribe T7 or Enzyme Solution | 4 μl |

To the sample obtained above, 2 μl of DNase was added, and DNase treatment was carried out by incubating at 37° C. for 15 minutes. Thereafter, phenol/chloroform was added thereto, followed by centrifugation at 15,000 rpm for 5 minutes, and supernatant was extracted with phenol/chloroform. To the obtained sample, 2.5 times the amount of this supernatant of ethanol and one tenth amount of 3 M sodium acetate were added, followed by centrifugation at 15,000 rpm for 15 minutes, and purification was carried out by ethanol precipitation.

Next, using denatured gel (6 M Urea 15% polyacrylamide gel), an RNA sample was subjected to PAGE purification. The RNA sample purified by ethanol precipitation was dissolved in 90% formamide (60 μl), and electrophoresis was carried out using denatured gel (6 M Urea 15% polyacrylamide gel). The object band was cut out and the gel was finely crushed with the tip of a pipette tip, and 400 μl of TE buffer was then added thereto and the obtained sample was stirred for an hour with a rotator. After centrifugation at 15,000 rpm for 5 minutes, RNA was extracted from the gel. Thereafter, purification was carried out by phenol/chloroform extraction and ethanol precipitation. The purity of the purified RNA samples was analyzed using denatured gel. Consequently, HRz1C was 38.8 μM, HRz2C was 35.8 μM, HRz1E was 17.0 μM and HRz2E was 8.91 μM.

Figure 4:
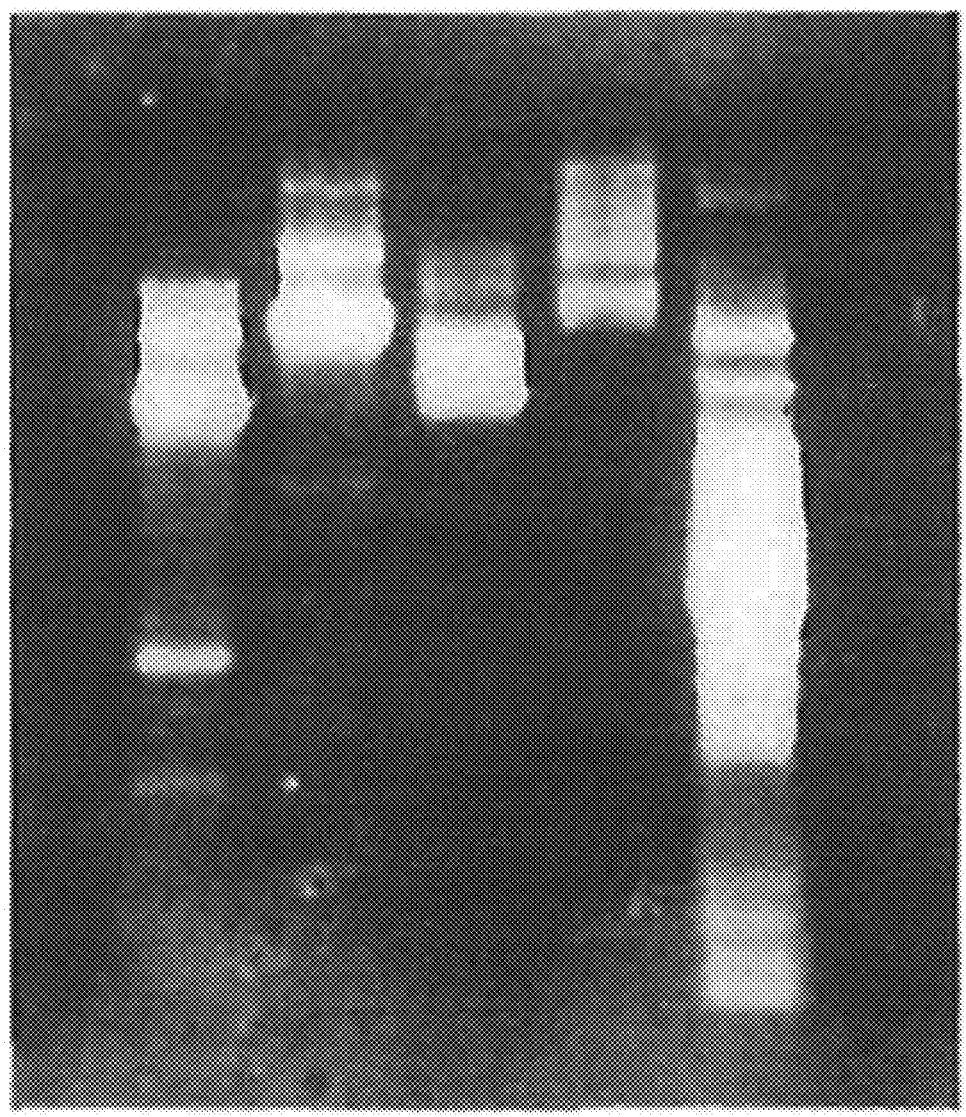
FIG. 4 is an electropherogram after synthesis of each ribozyme and substrate RNA (S).
Figure 5A:
FIG. 5A is an electropherogram after PAGE purification of each ribozyme (HRz1C, HRz2C, HRz1E and HRz2E) and substrate RNA (S).
Figure 5B:
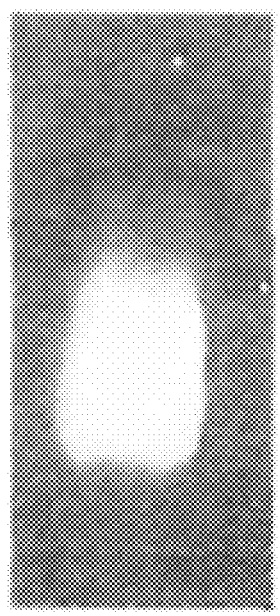
FIG. 5B is an electropherogram after PAGE purification of substrate RNA (S5).

FIG. 4 is an electropherogram after the T7 promoter reaction of each ribozyme (HRz1C, HRz2C, HRz1E, HRz2E and substrate RNA (S)). FIG. 5(A) and FIG. 5(B) are electropherograms of each ribozyme and substrate RNA (S) and S5 after PAGE purification.

In each ribozyme (HRz1C, HRz2C and HRz2E), the main band by PAGE purification was successfully cut out. In HRz1E, however, two bands were confirmed. In substrate S, meanwhile, the transcription reaction did not seem to effectively occur and thus S2, S3, S4 and S5 with a longer sequence were synthesized. As a result, it was revealed that S5 was most efficiently transcribed.

Subsequently, ribozyme activity was evaluated by EtBr staining. HRz1C (35 nt), HRz2C (41 nt), HRz1E (35 nt), HRz2E (41 nt) and a target sequence (S (35 nt)) constructed above were annealed by heating at 80° C. for 3 minutes and then gradually cooling to 25° C. over 15 minutes, and 20 mM MgCl$_2$ (4 μl) was then added to an annealing sample (36 μl) with the following composition, followed by incubating at 37° C. to carry out a cleavage reaction. Samples of the reaction solution were taken at each time point (0, 1, 2 and 24 hours) (4 μl and 8 μl each), and the taken samples of the reaction solution were purified by ethanol precipitation and then dissolved in 90% formamide, and cleaved bands were analyzed by electrophoresis using denatured gel (6 M Urea 15% polyacrylamide gel). The electropherograms were incorporated with a scanner and the cleavage ratio was calculated using image analysis software Image J.

TABLE 10

Table: Composition of annealing samples

| Material | Quantity |
|---|---|
| 5 μM HRz | 4 μl |
| 2.3 μM S5 | 10 μl |
| 10× cleavage buffer | 4 μl |
| H$_2$O | 24 μl |

Figure 6A:
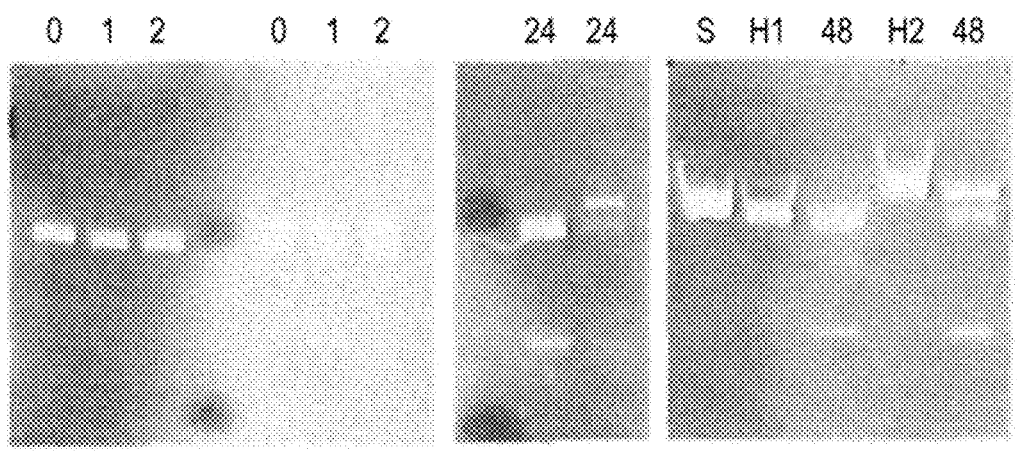
FIG. 6A is electropherograms showing activity evaluation (EtBr staining) of each ribozyme (H1: HRz1 and H2: HRz2) and a target RNA sequence (S).
Figure 6B:
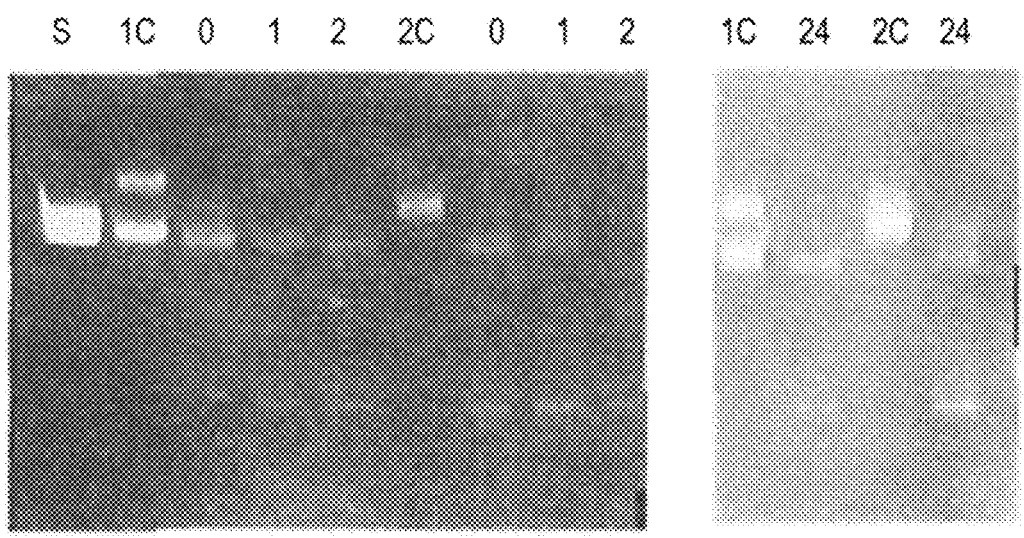
FIG. 6B is electropherograms showing activity evaluation (EtBr staining) of each ribozyme (H1: HRz1C and H2: HRz2C) and a target RNA sequence (S).

FIG. 6A and FIG. 6B are electropherograms showing activity evaluation over time (EtBr staining) of each ribozyme and the target RNA sequence (S). In FIG. 6A, H1 shows HRz1 and H2 shows HRz2. In FIG. 6A, H1 shows HRz1C and H2 shows HRz2C. Numbers show time (h).

FIG. 7 shows bar graphs showing the analytical results of cleaved bands by Image J and (A) shows the ratio of cleaved bands of HRz1E vs HRz1C, and (B) shows the ratio of cleaved bands of HRz2E vs HRz2C.

As a result of analysis, the cleaved bands of the target sequence were confirmed in all samples; however, it was revealed that the control cleaved the target sequence within a shorter time than HRz1 and HRz2. This is the result corresponding to prediction in which it is difficult to construct a ribozyme with high activity to the 5'-UAA-3' sequence only by a molecular design. To more specifically calculate the cleavage ratio, cleavage activity was evaluated by RI labeling.

Subsequently, in order to evaluate the cleavage activity of the ribozymes obtained above, the 5' end of substrate S was labeled with RI ($\gamma$-$^{32}$P) using T4 polynucleotide kinase (New England Biolabs).

First, to the sample obtained above, H$_2$O (79 μl), 10× Antarctic Phosphatase buffer (10 μl), 10 μM S (10 μl), and Antarctic Phosphatase (1 μl) were added, and the 5' end was dephosphorylated by incubating at 37° C. for an hour. Thereafter, the sample purified by phenol/chloroform extraction and ethanol precipitation was dissolved in 14 μl of H$_2$O, and Antarctic Phosphatase was inactivated by heating at 65° C. for 10 minutes using a block incubator.

Next, substrate S after dephosphorylation (14 μl), 10×T4 Polynucleotide Kinase Buffer (2 μl), ($\gamma$-$^{32}$P)ATP (2 μl), and T4 Polynucleotide Kinase (2 μl) were added thereto, followed by incubating at 37° C. for 30 minutes to label the 5' end with an isotope. After that, filtration with a filter was carried out using a spin column to remove unreacted ($\gamma^{32}$P)ATP (centrifugation at 8,000 rpm for a minute) and purification was carried out by ethanol precipitation. The sample purified by ethanol precipitation as described above was dissolved in 80% formamide, followed by electrophoresis using denatured (8 M urea, 15% polyacrylamide gel) gel. The object band was cut out and the gel was finely crushed by the tip of a pipette tip, and 300 μl of TE buffer was added thereto, followed by stirring with a rotator for an hour. Centrifugation was carried out at 15,000 rpm for 5 minutes and RNA was extracted from the gel and then purified by ethanol precipitation. The sample after purification was dissolved in 20 μl of TE to prepare substrate S with the radiolabeled 5' end.

TABLE 11

Table: Composition for dephosphorylation

| Material | Quantity |
|---|---|
| 10 μM HRz | 10 μl |
| 10× Antarctic Phosphatase buffer | 10 μl |
| Antarctic Phosphatase | 1 μl |
| H$_2$O | 79 μl |

TABLE 12

| Table: Composition for phosphorylation | |
|---|---|
| Material | Quantity |
| Dephosphorylated S5 | 14 μl |
| 10× T4 Polynucleotide Kinase Buffer | 2 μl |
| [gamma$^{32}$P]ATP | 2 μl |
| T4 Polynucleotide kinase | 2 μl |

The cleavage activity of the ribozymes obtained above was evaluated by the following method. To 2 μM ribozyme (10 μl), 10× cleavage buffer (2 μl), substrate S with the isotope-labeled 5' end (1 μl) and H$_2$O (5 μl) were added and the obtained mixture was heated at 80° C. for 3 minutes with a block incubator and then allowed to cool at room temperature for 10 minutes to carry out an annealing reaction, and 20 mM MgCl$_2$ was added thereto to start a reaction. After that, the cleavage reaction was carried out by incubating at 37° C. Samples were taken at each time point (1, 3 and 6 hours) (3.6 μl each), and to the taken solutions as samples, 0.4 μl of 0.5 M EDTA and 16 μl of formamide were added, and the obtained solution was heated at 80° C. for 3 minutes and then rapidly cooled for 2 minutes on ice. By centrifugation using denatured gel (8 M urea, 15% polyacrylamide gel), cleaved bands were analyzed.

Figure 8:
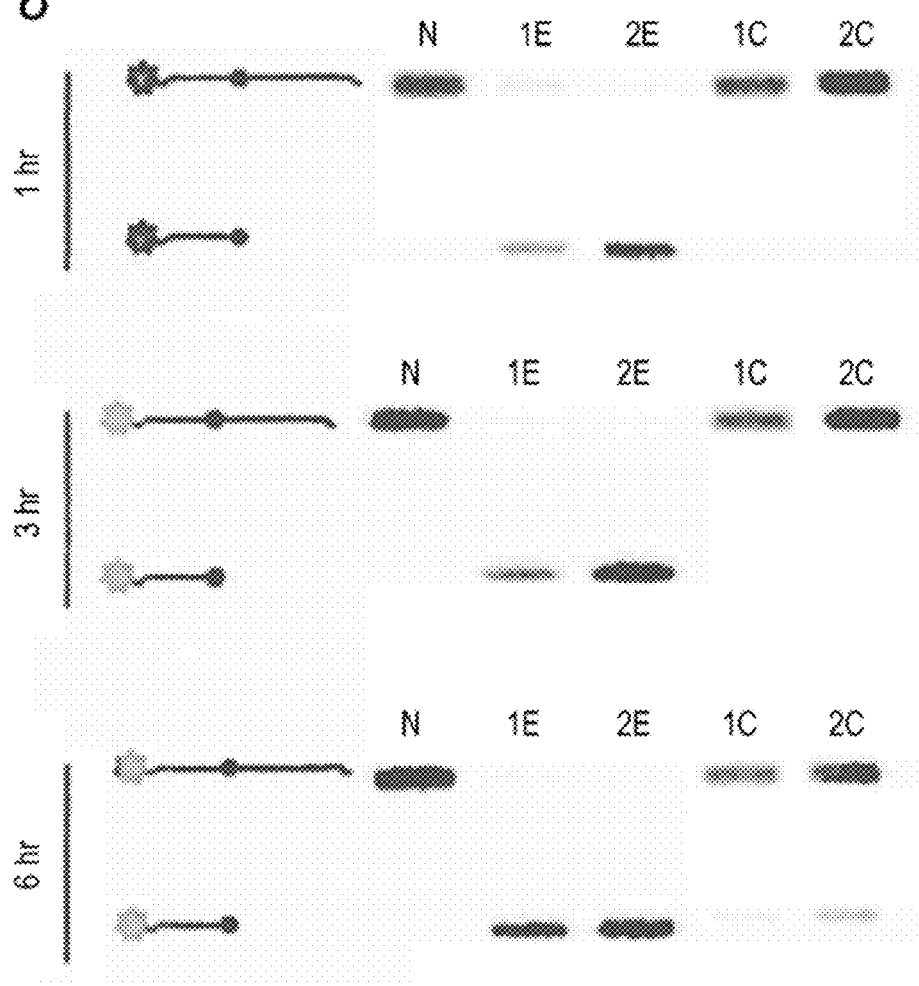
FIG. 8 is a diagram showing changes over time in the cleavage activity (RI labeling) of each ribozyme.
Figure 9:
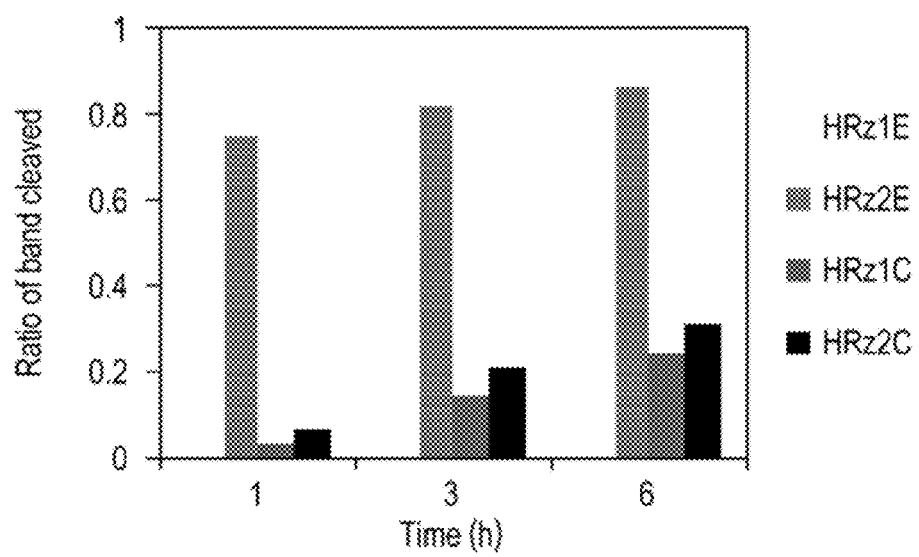
FIG. 9 is a bar graph showing the calculated results of chronological cleavage ratio of the cleavage activity (RI labeling) of each ribozyme in FIG. 8.

FIG. 8 is a diagram showing changes over time in the cleavage activity (RI labeling) of each ribozyme. FIG. 9 is a bar graph showing the calculated results of chronological cleavage ratio of the cleavage activity (RI labeling) of each ribozyme in FIG. 8.

EXAMPLE 3

In the present example, a ribozyme which cleaves the C site on HTR2C mRNA was constructed using an in vitro selection method. This in vitro selection method is one of the methods for constructing functional RNA (nucleic acid).

RNA can be converted to DNA by reverse transcription and DNA can also be amplified by PCR. Using this property, an RNA molecule having an object function was selected by a procedure as given below: (1) selection of an RNA molecule from RNA libraries under specific conditions (binding to a target molecule, showing activity etc.), (2) conversion of the RNA molecule selected in (1) to DNA by a reverse transcription reaction, and addition of the T7 promoter sequence and amplification by PCR, and (3) transcription to RNA by T7 RNA polymerase. An RNA molecule with a function to cleave the C site on HTR2C mRNA was obtained by repeating the operations (1) to (3).

As a basic skeleton, a hammerhead ribozyme derived from *Schistosoma mansoni* (Martick, M.; Scott, W. G. Cell 2006, 126, 309-20) was used. The selection method was designed from a reference (Persson, T., et. al. Chembiochem 2002, 3, 1066-71).

(Creation of Libraries H1 and H2)

Library H1 in which all 24 bases existing in an active region were randomized and Library H2 in which a 4 base loop was introduced into a target recognition region were designed.

The specific design of Library H1 is as shown below.

The specific design of Library H2 is as shown below.

Figure 10:
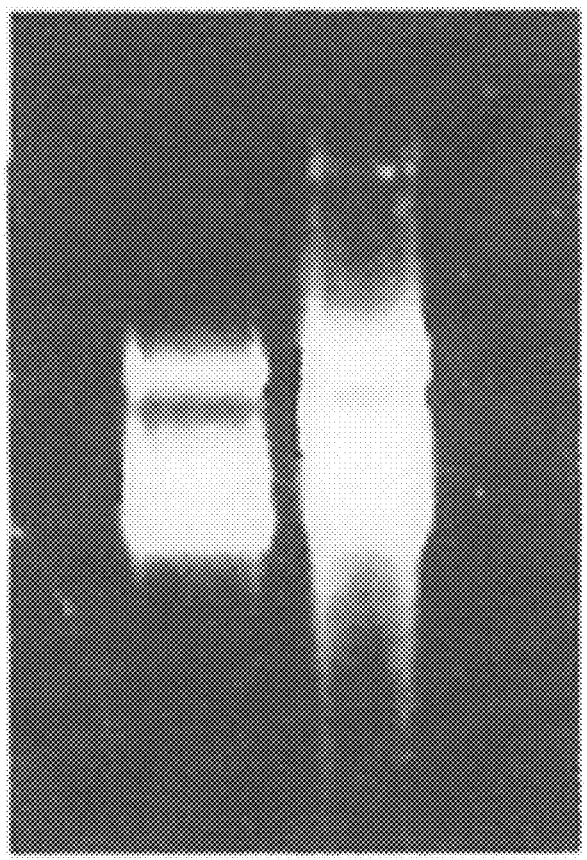
FIG. 10 is an electropherogram for confirmation of the creation of Libraries H1 and H2.

Library H (+) and Library H1 (−) or Library H2 (−) each were annealed and a template DNA was then adjusted using Klenow. The created double-stranded DNAs were used as templates, and Libraries H1 and H2 each were synthesized by an in vitro transcription reaction (FIG. 10).

The composition is as shown below (H1 and H2 both have the same composition).

TABLE 13

| Material | Quantity |
|---|---|
| RNase-Free Water | 66.4 μl |
| Template DNA | 53.6 μl |
| 10× AmpliScribe T7 Reaction Buffer | 32 μl |
| 2.5 mM NTP | 96 μl |
| 100 mM DTT | 32 μl |
| RiboGuard RNase Inhibitor | 8 μl |
| AmpliScribe T7 or Enzyme Solution | 32 μl |

The Libraries H1 and H2 obtained above were subjected to a selection treatment.

First, Libraries H1 and H2 and target RNA with the biotinylated 5' end each were annealed. Subsequently, magnet beads (Dynabeads M-280 streptavidin: DYNAL Invitrogen Corporation) washed with a washing buffer (10 mM HEPES, 5 mM EDTA, 50 mM NaCl) and the annealed sample were mixed and incubated at room temperature for 20 minutes to carry out a binding reaction of biotin and streptavidin (Round 1: 300 μl; Round 2 to 8: 50 μl).

TABLE 14

Table: Composition for annealing (Round 1)

| Material | Quantity |
|---|---|
| 5 μM library | 100 μl |
| 100 μM 5' end biotinylated S | 6 μl |
| 10× binding buffer | 12 μl |
| H$_2$O | 2 μl |

TABLE 15

Table: Composition for annealing (Round 2 to 8)

| Material | Quantity |
|---|---|
| 10 μM library | 10 μl |
| 10 μM 5' end biotinylated S | 12 μl |
| 10× binding buffer | 5 μl |
| H$_2$O | 23 μl |

To the sample obtained above, a cleaving buffer (50 mM Tris/HCl (pH 7.5), 50 mM NaCl, 20 mM MgCl$_2$) was added, followed by incubating at 37° C. for 30 minutes to activate a ribozyme. Here, a molecule with activity cleaves target RNA and is dissociated from magnet beads. After removing the magnet beads, the solution was purified by ethanol precipitation and dissolved in 6 μl of TE, and then conversion to cDNA by a reverse transcription reaction was carried out.

As the reverse transcription reaction, the selection sample (3 μl) and 20μ selection H RT (9.5 μl) were heated at 80° C. for 15 minutes and then left to stand at 25° C. for a minute and then cooled at 4° C. for annealing. The annealed sample thus obtained (12.5 μl) was mixed with 5× buffer (4 1), 10 mM dNTP (2 1) and AMV RTase (1.5) and the obtained sample was heated at 42° C. for 15 minutes and then heated at 99° C. for 5 minutes and then cooled to 4° C. to carry out the reverse transcription reaction.

Thereafter, DNA as a template was amplified by PCR. PCR was carried out as a cycle of heating at 95° C. for 15 seconds, at 55° C. for 30 seconds then heating at 68° C. for 30 seconds using the following composition.

TABLE 16

Table: Composition of PCR mix

| Material | Quantity |
|---|---|
| 10× Thermo Pol Reaction Buffer | 10 μl |
| 2.5 mM dNTP | 12 μl |
| 5 μM H(+) | 6 μl |
| 5 μM selection H RT | 6 μl |
| Template DNA | 2 μl |
| Taq Polymerase | 0.5 μl |
| H$_2$O | 67.5 μl |

At this time, in order to determine the optimal PCR conditions, a cycle check was carried out in the same conditions as the above PCR. The cycle check was carried out by taking samples at every 5 cycles till 10 to 35 cycles in Round 1 to 3 and taking samples at every 4 cycles till 8 to 24 cycles in Round 4 to 8.

Figure 11A:
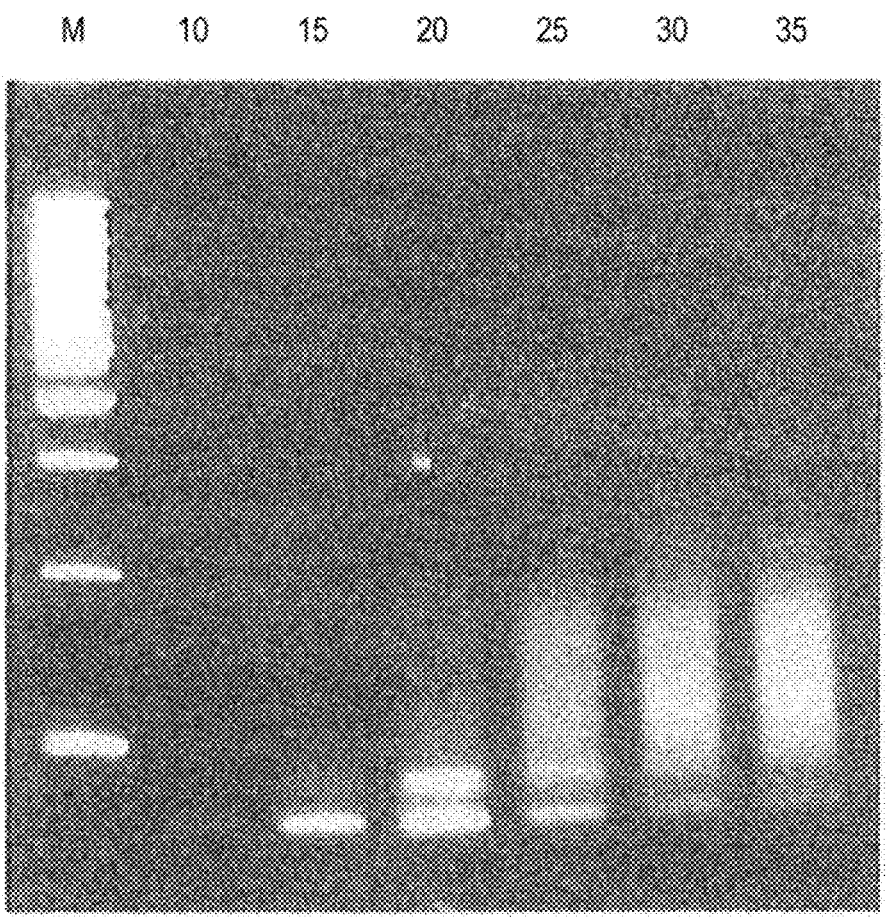
FIG. 11A is an electropherogram showing the cycle check results of Round 1.
Figure 11B:
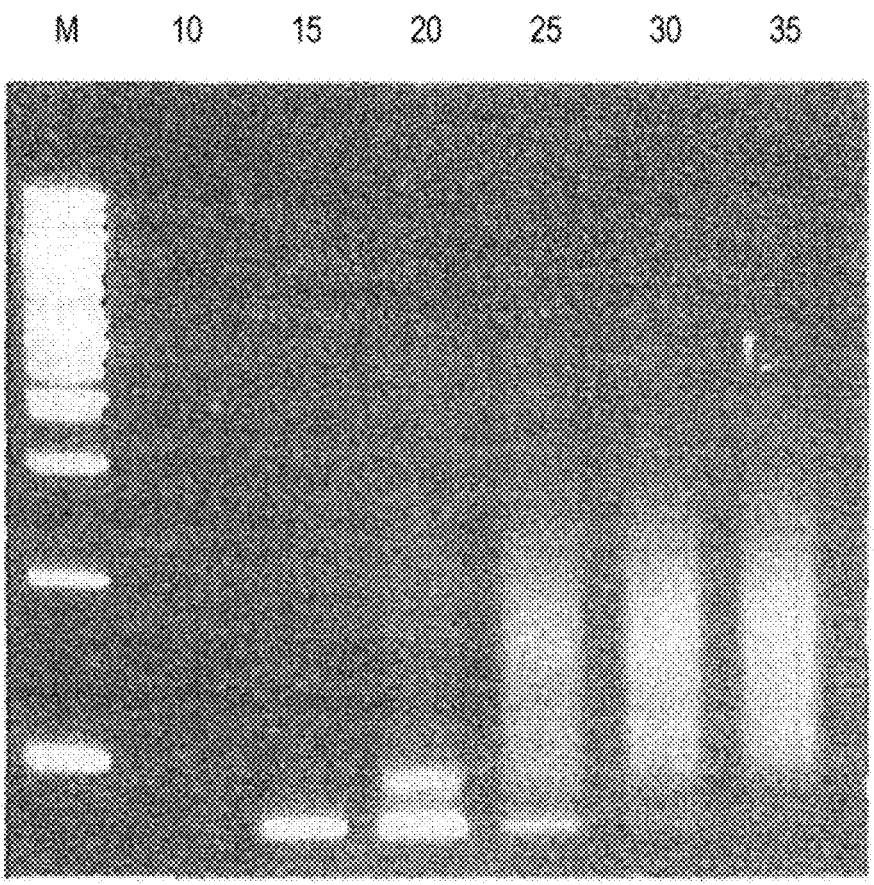
FIG. 11B is another electropherogram showing the cycle check results of Round 1.

FIG. 11A and FIG. 11B are electropherograms each showing the results of cycle checks in Round 1. In the diagrams, the left half shows Library H1 and the right half shows Library H2.

The sample after amplification was purified by phenol/chloroform extraction and ethanol precipitation and then dissolved in 10 μl of TE, and using 5 μl in 10 μl as template DNA, an RNA library to be used in the next round was synthesized by an in vitro transcription reaction (heating at 37° C. for 3 hours).

TABLE 17

Table: Composition for in vitro transcription reaction

| Material | Quantity |
|---|---|
| RNase-Free Water | 2.5 μl |
| Template DNA | 5 μl |
| 10× AmpliScribe T7 Reaction Buffer | 2 μl |
| 2.5 mM NTP | 6 μl |
| 100 mM DTT | 2 μl |
| RiboGuard RNase Inhibitor | 0.5 μl |
| AmpliScribe T7 or Enzyme Solution | 2 μl |

The operation was repeated 8 times, and from the results of cycle checks, it was anticipated that molecular species converged, and thus the sequences of RNA molecules were analyzed (FIG. 12: the left half shows Library H1 and the right half shows Library H2). The sequence analysis results of Library H1 are as shows in FIG. 13 and the sequence analysis results of Library H2 are as shown in FIG. 14.

From the sequence analysis results, 10/16 was a shorter fragment than the basic skeleton in Library H1. As the other molecules, ribozymes in which the sequence of the cleavage site is shifted from the C site by a base in order to accord with the 5'-N'HH'-3' rule were obtained. In Library H2, since molecular species did not converge much, in vitro selection was subsequently carried out. Since a decrease in the number of PCR cycles after the reverse transcription reaction in Round 12 was observed, the sequence was analyzed once again. The sequence reanalysis results are shown in FIG. 15.

Among the sequences of 36 molecules confirmed by sequence analysis for a second time, convergence was observed in 3 molecules shown in FIG. 15. The activity of these 3 molecules was evaluated (RI labeling) and the cleavage activity to HTR2C mRNA was not shown at all. Therefore, a sequence (5'-CUGA-3') which exists in the active region and is essential for the cleavage activity was fixed so that only a ribozyme which cleaves the C site could be selected, and RNA libraries (2H1 and 2H2) in which other sequences were diversified were redesigned.

To the sample synthesized above, 1 µl of DNase I was added, followed by incubating at 37° C. for 15 minutes for DNase treatment. After that, purification was carried out by phenol/chloroform extraction and ethanol precipitation. In addition, in order to remove unreacted NTP, the sample after purification was dissolved in 40 µl of TE, followed by gel filtration. As a method thereof, centrifugation was carried out at 3,200 rpm for 4 minutes using Micro Bio-Spin 30 Colum in RNase Free. The concentration of the sample after gel filtration was determined using Nanovue and the next round was carried out.

(Incubation of restriction enzyme site)

In order to incubate a restriction enzyme in a DNA library amplified by PCR in Round 8, PCR was carried out using two types of primers, HH-Fw and HH-Rv. At this time, in order to determine the optimal PCR conditions, a cycle check was carried out. The cycle check was carried out using the following composition by heating at 95° C. for 15 seconds and then 55° C. for 30 seconds and subsequently heating treatment at 68° C. for 30 seconds, and samples were taken at every 2 cycles till Round 2 to 10. Consequently, the optimal conditions were Round 6 and thus a restriction enzyme was incubated using the following composition.

TABLE 18

Table: Composition used in cycle checks

| Material | Quantity |
|---|---|
| 10× Thermo Pol Reaction Buffer | 5 µl |
| 2 mM dNTP | 5 µl |
| 5 µM HH-Fw | 3 µl |
| 5 µM HH-Rv | 3 µl |
| Template DNA | 1 µl |
| Taq Polymerase | 0.25 µl |
| $H_2O$ | 32.5 µl |

TABLE 19

Table: Composition used for incubation of restriction enzyme

| Material | Quantity |
|---|---|
| 10× Thermo Pol Reaction Buffer | 10 µl |
| 2 mM dNTP | 10 µl |
| 5 µM HSeq_F | 6 µl |
| 5 µM HHSeq_R | 6 µl |
| Template DNA | 2 µl |
| Taq Polymerase | 0.5 µl |
| $H_2O$ | 65.5 µl |

After amplification, the sample was purified by phenol/chloroform extraction and ethanol precipitation and dissolved in 20 µl of TE.

The restriction enzyme treatment was carried out at 37° C. for 2 hours using the following composition, followed by phenol/chloroform extraction, and purification was then carried out by ethanol precipitation.

TABLE 20

Table: Composition for restriction enzyme treatment

| Material | Quantity |
|---|---|
| $H_2O$ | 161.5 µl |
| 10× H buffer | 20 µl |
| DNA library | 16 µl |
| BamH I | 2 µl |
| EcoR I | 0.5 µl |

As the results of concentration determination by Nanovue after the treatment, DNA library H1 was 0.020 µg/µl and DNA library H2 was 0.020 µg/µl.

(Restriction enzyme treatment of vectors)

pBluescript (0.245 µg/µl) was subjected to restriction enzyme treatment using a composition containing BamH I and EcoR I at 37° C. for 2 hours. After the treatment, purification was carried out by phenol/chloroform extraction and ethanol precipitation. After the treatment, the result of concentration determination by Nanovue was 0.041 µg/µl.

TABLE 21

Table: Composition used for restriction enzyme treatment

| Material | Quantity |
|---|---|
| $H_2O$ | 161.5 µl |
| 10× H buffer | 20 µl |
| DNA library | 16 µl |
| BamH I | 2 µl |
| EcoR I | 0.5 µl |

(Ligation)

pBluescript and DNA libraries (H1, H2) were ligated at 16° C. for 4 hours 31 minutes. The molar ratio of pBluescript and a DNA library was 1:3. After that, the sample was purified by phenol chloroform extraction and ethanol precipitation and then dissolved in 3 µl of $H_2O$.

TABLE 22

Table: Composition for ligation

| Material | Quantity |
|---|---|
| DNA library | 0.5 µl |
| pBluescript | 0.5 µl |
| Ligation mix | 3 µl |

(Electroporation)

To dissolved JM83, 1.5 µl in 3 µl of the sample after ligation was added on ice and the obtained sample was transferred to an electrocuvette and subjected to electroporation. Immediately after that, the obtained sample was poured in SOC and cultured at 37° C. for 30 minutes. The sample after culturing was seeded in LB medium (containing ampicillin and X-gal) and cultured at 37° C. overnight.

(Colony PCR)

After culturing overnight, among blue colonies and white colonies, only white colonies of DNA libraries H1 and H2 were picked up and 24 colonies each were put into a PCR tube using a toothpick. A PCR mix with the following composition was poured into the tube in a volume of 10 µl each.

TABLE 23

| Table: Composition of PCR mix (for 50 tubes) | |
|---|---|
| Material | Quantity |
| 10× Thermo Pol Reaction Buffer | 50 μl |
| 2 mM dNTP | 50 μl |
| 5 μM M13-Fw | 30 μl |
| 5 μM M13-Rv | 30 μl |
| Taq Polymerase | 2.5 μl |
| H$_2$O | 337.5 μl |

The heating treatment at 95° C. for 15 seconds, at 55° C. for 30 seconds and at 68° C. for 30 seconds was considered as a cycle and PCR was carried out 30 cycles, followed by 1% agarose electrophoresis for confirmation whether an object amplified sample was obtained. Of DNA libraries H1 and H2, 18 samples each were selected and subjected to sequence PCR.

After sequence PCR, the sample was purified by ethanol precipitation and dissolved in 3 μl of a mixed solution of formamide and blue dextran (5:1). The sample was heated at 95° C. for 3 minutes and then rapidly cooled on ice. After that, a base sequence was analyzed by ABI377.

EXAMPLE 4

In the present example, a ribozyme (HRzC-ino) identifying A-to-I editing at the C site on HTR2C mRNA was designed.

A basic skeleton was HRz2E, and adenosine at the C site is recognized by forming a base pair with uridine existing in the target recognition region of HRzC. Therefore, utilizing that inosine forms a base pair with cytosine, uridine base-pairing with the C site was substituted by cytosine to design a ribozyme HRzC-ino showing cleavage activity only when the C site is subjected to A to I editing.

The specific sequence of the ribozyme HRzC-ino (41 nt) is as shown in the following formula (5).

[Chem. 20]

(5)
(SEQ ID NO: 1)
5'-GAAUAGGAC|CUGAUGAGGCCGAAAGGCCGAA|ACGUAUUGCU-3'

Figure 16:
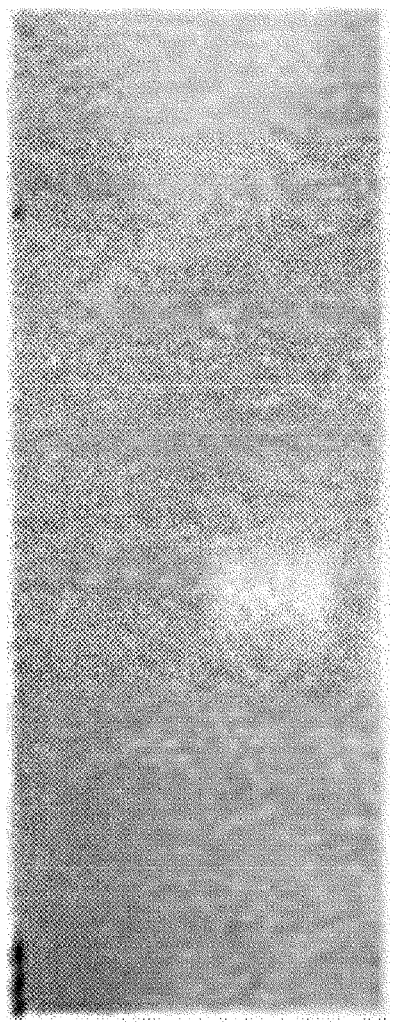
FIG. 16 is an electropherogram for confirmation after synthesis of a ribozyme HRzC-ino.

Based on the ribozyme HRzC-ino designed as above, the ribozyme (HRzC-ino) identifying A-to-I editing at the C site on HTR2C mRNA was synthesized. Although the final concentration was low (2.3 μM), HRzC-ino was obtained (FIG. 16).

Figure 17:
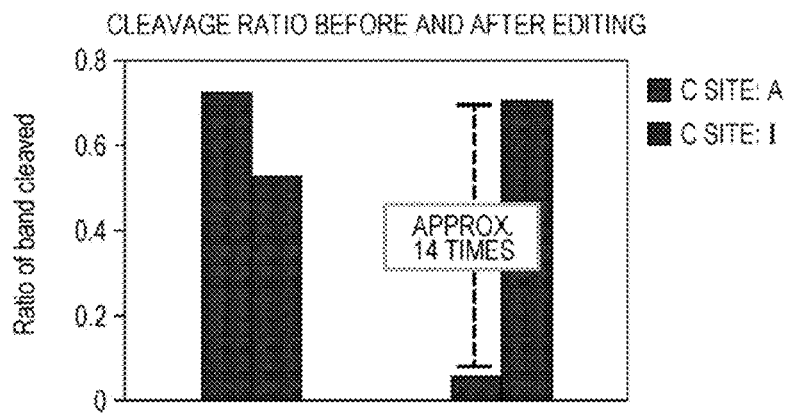
FIG. 17 is a graph showing the calculated results of cleavage ratio of the ribozyme HRzC-ino.

The activity of the ribozyme HRzC-ino obtained above was evaluated (RI labeling). Using substrate S and S C-ino, in which the C site of S is inosine (I), as target RNAs, the cleavage activity to each target RNA was compared (FIG. 17). The method for labeling the 5' end of target RNA and the method for evaluating activity were carried out in the same method as shown above.

The cleavage activity of the ribozyme HRzC-ino was evaluated as above. The results confirmed that higher cleavage activity was shown to a sequence in which the C site is the base I than that in which it is the base A (approximately 14 times). The above results showed that the ribozyme HRzC-ino could specifically identify A-to-I editing at the C site in HTR2C mRNA.

EXAMPLE 5

In the present example, the in vitro trans cleavage activity and specificity of an A-to-I editing-specific ribozyme to a HTR2C RNA fragment were examined.

In order to evaluate the cleavage activity and editing specificity of HR-HTR2C-edit, an in vitro assay was carried out using a synthetic HTR2C RNA fragment containing the C site. In this assay, two types of $^{32}$P labeled HTR2C mRNA fragments (37 nucleotides), i.e. two types, one fragment with the base A at the C site as an unedited substrate (HTR2C-ade) and another fragment with the base I at the C site as an edited substrate, were used (FIG. 18A).

The substrate RNA was transcribed in vitro and annealed in the presence of an excessive amount of gel-purified ribozymes HR-HTR2C and HR-HTR2C-edit. The cleavage reaction was begun by the addition of 20 mM MgCl$_2$ at 37° C. After an hour, cleaved bands were analyzed using gel electrophoresis and a cleavage rate was calculated (FIG. 18B and 18C). In HR-HTR2C, similar cleavage rates to HTR2C-ade and HTR2C-ino (0.69 and 0.59) were observed. In contrast, the cleavage rate of HR-HTR2C-edit to HTR2C-ino was remarkably higher than the cleavage rate to HTR2C-ade (0.76 and 0.09). These results show that A-to-I editing-specific cleavage activity is provided by forming HR-HTR2C-edit by converting a second base on HR-HTR2C.

Next, in order to analyze cleavage kinetics for ribozymes, the trans cleavage rate constant was determined under single turnover conditions using the above-described experimental method (FIG. 19). FIG. 19A shows changes over time in cleavage products obtained by the reaction of HR-HTR2C-edit to HTR2C-ade (the upper diagram of FIG. 19A) and HTR2C-ino (the lower diagram of FIG. 19A). The kinetic analysis results of HR-HTR2C-edit showed high $k_{cat}$ values (0.67±0.011 min$^{-1}$) when using HTR2C-ino and low $k_{cat}$ (0.01±0.001 min$^{-1}$) values when using HTR2C-ade (FIG. 19B, Table 3). Contrarily, in HR-HTR2C, catalytic activity about the cleavage of both edited and unedited substrates was shown using $k_{cat}$ values (0.05±0.001 min$^{-1}$, 0.44±0.022 min$^{-1}$) A difference in $k_{cat}$ values on this ribozyme was smaller than that on HR-HTR2C-edit. The fractions of products at the final point (F∞) of reactions are similar when combinations of the recognition base and the modification site are U-A (0.74), U-I (0.63) and C-I (0.85), and in C-A, a significantly low value (0.23) was shown.

This result corresponded to the result of previous research (Werner, M., et al. 1995. Nucleic Acids Res 23(12): 2092-2096) and it was found that the formation of a base pair by a recognition base affected and really had an influence on the cleavage activity of HR-HTR2C-edit. In HR-HTR2C, a difference of cleavage activity between U-A and U-I seemed to follow the order which accords with the thermal stability of a base pair and the stability of a U-I base pair was lower than that of a U-A base pair (Serra, M. J., et al. 2004. Nucleic Acids Res 32(5): 1824-1828). These results showed that the editing-specific cleavage activity of ribozymes could be designed by combining a recognition base and a base at a target modification site.

EXAMPLE 6

In the present example, C-to-U editing-specific cleavage to APOB RNA using a ribozyme was examined. In order to determine if a ribozyme produced in the present invention can be applied to specific cleavage of other forms of RNA substitution editing, a C-to-U editing-specific ribozyme was constructed by changing a recognition base. The C-to-U editing-specific ribozyme was designed as a target to APOB mRNA by converting a glutamine codon (CAA) to an in-frame stop codon by C-to-U editing in the base C at position 6666 of APOB mRNA. Using the same method as for A-to-I editing, HHR was constructed using a core sequence with the same catalytic activity to cleave C-to-U modification site at the 5' position on APOB mRNA. A C-to-U editing-specific ribozyme (HR-APOB-edit) was created by introducing a base A into a recognition nucleotide to form a base pair with the base U from C-to-U editing of APOB RNA. The cleavage activity of HR-APOB-edit to an unedited substrate (APOB-cyt) and an edited substrate (APOB-uri) was analyzed by an in vitro cleavage assay (FIG. 20B). As shown in FIG. 20B, the cleavage of APOB-uri was considerably larger than the cleavage of APOB-cyt after the cleavage reaction for an hour in the presence of an excessive amount of the ribozyme. In kinetic analysis to HR-APOB-edit, the cleavage rates of HR-APOB-edit to APOB-cyt and APOB-uri were significantly different (0.01±0.006 min$^{-1}$ and 0.17±0.008 min$^{-1}$) (FIG. 20C). Besides, in the product fraction at the final point, a distinct difference between APOB-cyt and APOB-uri was observed. These data showed that the selection of combinations of a recognition base and a target modification site can be applied to the construction of a ribozyme for not only A-to-I mutation-specific cleavage but also C-to-U editing-specific cleavage.

EXAMPLE 7

In the present example, in order to examine A-to-I editing-specific cleavage to FLNA mRNA extracted from cells and synthetic FLNA mRNA, the effectiveness of A-to-I editing-specific cleavage to mRNA extracted from cells was evaluated.

FLNA mRNA containing a conserved A-to-I modification site (Q/R site) was used as target mRNA in which endogenous FLNA mRNA is edited and adenosine deaminase (ADAR2) acting on RNA 2 is excessively expressed in a cell (Nishimoto, Y., et al. 2008. Neurosci Res 61(2): 201-206). A ribozyme for editing-specific cleavage of FLNA mRNA (HR-FLNA-edit) was designed using the above-described method and the cleavage activity and editing specificity of HR-FNLA-edit were analyzed by an in vitro cleavage assay using a synthetic FLNA RNA fragment (FIG. 22). The cleavage rate constant and fraction of products at the final point of HR-FLNA-edit to an edited FLNA RNA fragment were much larger than those to an unedited FLNA RNA fragment (FIG. 22, Table 3). These results were similar to the results observed in HR-HTR2C-edit.

Figure 23B:
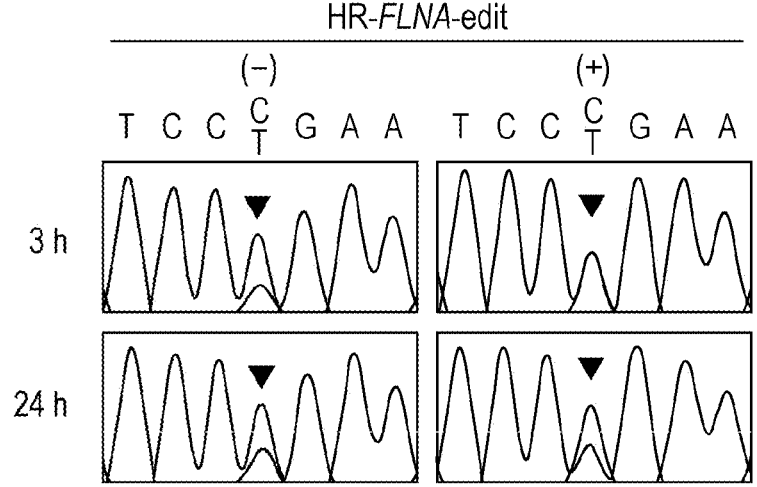
FIG. 23B is a diagram showing in vitro A-to-I editing-specific cleavage of a ribozyme to FLNA mRNA extracted from cells (sequence chromatograms of products by the presence or absence of cleavage reaction of HR-FLNA-edit).
Figure 24:
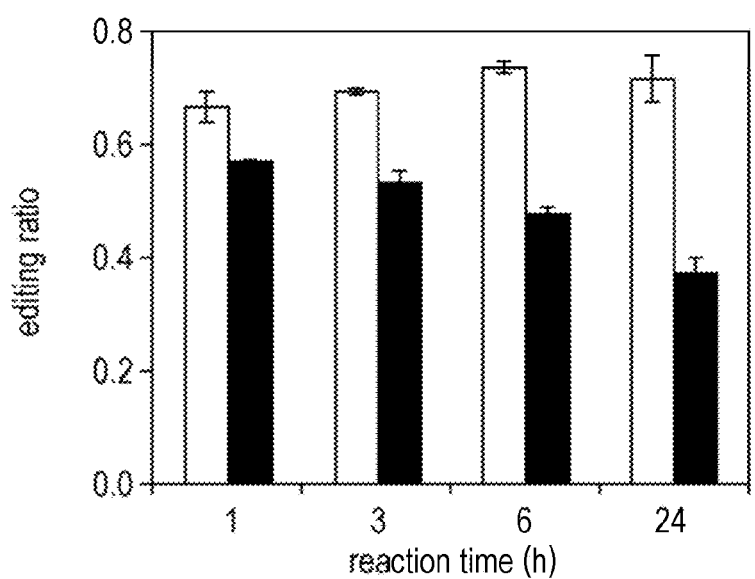
FIG. 24 is a graph showing the quantitative results of the editing ratio of HR-FLNA fragments after reaction with a ribozyme.

Next, in order to evaluate the efficiency of editing-specific cleavage for HR-FLNA-edit to FLNA mRNA extracted from cells, an edited FLNA mRNA was prepared from HEK293 cells excessively expressing ADAR2. The present inventor already established Tet-ADAR2 cells which can be stably transfected by the ADAR2 expression vector containing an expression system which can induce doxycycline (Dox). The whole RNA containing a mixture of edited FLNA mRNA and unedited FLNA mRNA could be obtained from Tet-ADAR2 cells cultured using Dox at any concentration. If a ribozyme specifically cleaves edited FLNA mRNA in the whole RNA extracted, the ratio of edited FLNA mRNA and unedited FLNA mRNA must be lowered. Therefore, the efficiency of editing-specific cleavage was evaluated by measuring a difference between a sample containing a ribozyme with a difference in the editing ratio at the Q/R site and a sample not containing it. The experiment scheme to quantify the editing ratio is shown in FIG. 23A. First, 150 ng of extracted RNA was annealed using an excessive amount of HR-FLNA-edit (the final concentration: 2.5 µM) and cleavage reactions were carried out in a buffer with 20 mM MgCl$_2$. After cleavage reactions for different times (1, 3, 6 and 24 hours), RNA samples were subjected to RT-PCR using an FLNA specific primer and PCR fragments were directly sequenced using a fluorescent dideoxy sequencing method (FIG. 23A). In order to quantify an editing ratio at the Q/R site in each sample, the peak heights of T and C were measured by a chromatogram created for sequences amplified using a reverse primer (FIG. 23B). The editing ratio decreased depending on the length of the HR-FLNA-edit reaction. That is, the editing ratios were 0.56, 0.52, 0.47 and 0.36 per 1, 3, 6 and 24 hours respectively and these values were low compared with reactions not containing a ribozyme. The peak height of the A/G mixture was much more discordant than the peak height of the T/C mixture, however, a decrease in the editing ratio depending on reaction time in the presence of a ribozyme was evaluated by measuring the editing ratio in each reaction using a forward primer (FIG. 24). These results showed that HR-FLNA-edit editing-specifically cleaves FLNA mRNA extracted from cells.

In the present invention, as described above, in order to construct an editing-specific ribozyme, the ribozyme was designed so that the recognition base of the ribozyme would form a base pair with only a modified base of target RNA, and thus it was shown that the ribozyme thus designed is very effective in RNA editing-specific cleavage. The ribozyme designed for A-to-I editing-specific cleavage had catalytic activity to edited HTR2C and an edited FLNA RNA fragment which is 10 or more times as high as that to unedited RNA. Similarly, it was also revealed that a ribozyme for C-to-U editing of APOB RNA had very high catalytic activity to an edited APOB RNA fragment. The results by an in vitro cleavage assay in the present invention showed that the editing-specific hammerhead ribozyme (HHR) according to the present invention has selective cleavage activity to edited target RNA. When dynamic analytical data of the hammerhead ribozyme (HHR) of the present invention to an edited substrate were compared, it was revealed that the cleavage rate of HR-HTR2C-edit is much higher than that of HR-FLNA-edit and HR-APOB-edit. On the other hand, a product fraction at each final point of reaction was same. It is believed that these differences in cleavage rates depend on hybridizing arms and sequences of base pairs thereof. As shown in mutation analysis at a place corresponding to the recognition base of HHR (e.g. Zoumadakis, M., et al. 1994. Nucleic Acids Res 22(24): 5271-5278), the target cleavage activity of the HHR of the present invention is controlled based on whether the recognition base can form a base pair with a modified base of target RNA. In addition, the data of HR-HTR2C having U-A and U-I base pairs also show that cleavage activity is affected by the thermal stability of a base pair at the recognition base. These results suggest that the present invention can be applied to specific cleavage of not only RNA substitution editing but also other forms of base substitution including point mutation, single nucleotide polymorphism (SNP) and the like by selecting an appropriate combination of a recognition base and a target base.

As with the present invention, the conversion of a recognition base of a ribozyme is useful in designing editing-specific and mutation-specific cleavage and the like even if cleavage activity thereof is restricted by the triplet rule. In the present invention, the cleavage sites of all target RNA shown as examples were selected in order to accord with the triplet rule retaining the cleavage activity of ribozymes. Since HHR has N'HH' cleaving specificity, the present invention cannot be applied when a nucleotide at one base or two bases upstream on the 5' side of the mutation site in a target sequence is G. For the same reason, it is impossible to identify all combinations of mutations even by using a method for recognizing mutants by HHR which applies N'HH' specificity. However, when a ribozyme is designed based on a strategy adopted in the present invention considering which base is a target mutation site or which bases exist in the front and back of a surrounding sequence thereof, almost all of substitution of nucleotides can be specifically recognized by an artificial ribozyme. By the spread of target mutation specificity as described above, it is possible to expand a possibility that a ribozyme can be applied to mutation in which gene expression is selectively suppressed or to substitution editing.

Further, the present invention shows that editing-specific cleavage by a ribosome can be applied in vitro to not only short RNA fragments but also physiological mRNA. In the present invention, the effectiveness of editing-specific cleavage of cell-derived target mRNA was evaluated as changes in the editing ratio utilizing the peak height of a modification site based on DNA sequence chromatogram. When the editing-specific cleavage of HR-FLNA-edit was analyzed by this method, although the total amount of FLNA mRNA is needed to quantify, by roughly estimating, 51% of FLNA mRNA was cleaved by HR-FLNA-edit in a reaction over 24 hours. The amount of editing-specific cleavage depended on reaction time. The cleaving efficiency was, however, low compared to the reaction to FLNA mRNA fragments and almost saturated states were obtained by the cleavage reaction to FLNA mRNA fragments over an hour (FIGS. 22 and 23).

Industrial Applicability

To sum up, in the present invention, utilizing the framework of the smallest hammerhead liposome (HHR), the design and creation of ribozymes for cleaving target RNA based on A-to-I and C-to-U RNA substitution editing have been developed. The basic framework of the ribozyme design of the present invention is to produce a ribozyme showing high specific cleavage activity to both synthetic edited RNA fragments and physiological mRNA by converting the recognition base of ribozymes. Further, the strategy of the present invention can be widely applied to not only RNA substitution editing but also other forms of mutation, for example, modification such as substitutions, deletions and additions of bases including mutation, such as SNP by selecting specific combinations of a recognition base and a target base. Therefore, the present invention is expected to be useful for the research and development of new drugs which contribute to prevention and treatment of not only disorders caused by RNA editing and the like but also disorders caused by other forms of modification such as mutation.

SEQUENCE LISTING

```
<160> NUMBER OF SEQ ID NOS: 68

<210> SEQ ID NO 1
<211> LENGTH: 41
<212> TYPE: RNA
<213> ORGANISM: Artificial Sequence
<220> FEATURE:
<223> OTHER INFORMATION: Chem.11

<400> SEQUENCE: 1
gaauaggacc ugaugaggcc gaaaggccga aacguauugc u                41

<210> SEQ ID NO 2
<211> LENGTH: 41
<212> TYPE: RNA
<213> ORGANISM: human

<400> SEQUENCE: 2
ggaucgguau guagcaauac guaauccuau ugagcauagc c                41

<210> SEQ ID NO 3
<211> LENGTH: 41
<212> TYPE: RNA
<213> ORGANISM: Artificial Sequence
<220> FEATURE:
<223> OTHER INFORMATION: Chem.12

<400> SEQUENCE: 3 cugacuccc ugaugaggcc gaaaggccga aaaggcuaga a                 41

<210> SEQ ID NO 4
<211> LENGTH: 23
<212> TYPE: RNA
<213> ORGANISM: human

<400> SEQUENCE: 4
uucuagccuu caggagucag ggc                                    23

<210> SEQ ID NO 5
<211> LENGTH: 41
<212> TYPE: RNA
<213> ORGANISM: Artificial Sequence
```

<220> FEATURE:
<223> OTHER INFORMATION: Chem.13

<400> SEQUENCE: 5
aucaaauuac ugaugaggcc gaaaggccga aaucauauau g                           41

<210> SEQ ID NO 6
<211> LENGTH: 28
<212> TYPE: RNA
<213> ORGANISM: Artificial Sequence
<220> FEATURE:
<223> OTHER INFORMATION: Chem.13

<400> SEQUENCE: 6
gcagacauau augauacaau uugaucag                                          28

<210> SEQ ID NO 7
<211> LENGTH: 23
<212> TYPE: RNA
<213> ORGANISM: Artificial Sequence
<220> FEATURE:
<223> OTHER INFORMATION: Helix II
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or u

<400> SEQUENCE: 7
cugancgagg ccgaaaggcc gaa                                               23

<210> SEQ ID NO 8
<211> LENGTH: 59
<212> TYPE: DNA
<213> ORGANISM: Artificial Sequence
<220> FEATURE:
<223> OTHER INFORMATION: HR-HTR2C in table3

<400> SEQUENCE: 8
agcaatacgt tcggcctttt cggcctcatc agatcctatt ctatagtgag tcgtattag        59

<210> SEQ ID NO 9
<211> LENGTH: 59
<212> TYPE: DNA
<213> ORGANISM: Artificial Sequence
<220> FEATURE:
<223> OTHER INFORMATION: HR-HTR2C-edit in table3

<400> SEQUENCE: 9
agcaatacgt tcggcctttt cggcctcatc aggtcctatt ctatagtgag tcgtattag        59

<210> SEQ ID NO 10
<211> LENGTH: 31
<212> TYPE: DNA
<213> ORGANISM: Artificial Sequence
<220> FEATURE:
<223> OTHER INFORMATION: HR-ApoB-edit_F in table3

<400> SEQUENCE: 10
ctaatacgac tcactatagg gatcaaatta c                                      31

```
<210> SEQ ID NO 11
<211> LENGTH: 49
<212> TYPE: DNA
<213> ORGANISM: Artificial Sequence
<220> FEATURE:
<223> OTHER INFORMATION: HR-ApoB-edit_R in table3

<400> SEQUENCE: 11
catatatgat tcggccttt cggcctcatc agtaatttga tccctatag                49

<210> SEQ ID NO 12
<211> LENGTH: 29
<212> TYPE: DNA
<213> ORGANISM: Artificial Sequence
<220> FEATURE:
<223> OTHER INFORMATION: HR-FLNA-edit_F in table3

<400> SEQUENCE: 12
ctaatacgac tcactatagg gctgactcc                                     29

<210> SEQ ID NO 13
<211> LENGTH: 49
<212> TYPE: DNA
<213> ORGANISM: Artificial Sequence
<220> FEATURE:
<223> OTHER INFORMATION: HR-FLNA-edit_R in table3

<400> SEQUENCE: 13
ttctagcctt ttcggccttt cggcctcatc aggggagtca gccctatag               49

<210> SEQ ID NO 14
<211> LENGTH: 41
<212> TYPE: RNA
<213> ORGANISM: Artificial Sequence
<220> FEATURE:
<223> OTHER INFORMATION: HTR2C-ino in table3
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or u

<400> SEQUENCE: 14
ggaucgguau guagcaauac guanuccuau ugagcauagc c                       41

<210> SEQ ID NO 15
<211> LENGTH: 28
<212> TYPE: RNA
<213> ORGANISM: human

<400> SEQUENCE: 15
gcagacauau augauauaau uugaucag                                      28

<210> SEQ ID NO 16
<211> LENGTH: 28
<212> TYPE: RNA
<213> ORGANISM: Artificial Sequence
<220> FEATURE:
<223> OTHER INFORMATION: ApoB-cyt in figure20

<400> SEQUENCE: 16
gcagacauau augauacaau uugaucag                                      28
```

```
<210> SEQ ID NO 17
<211> LENGTH: 23
<212> TYPE: RNA
<213> ORGANISM: Artificial Sequence
<220> FEATURE:
<223> OTHER INFORMATION: FLNA-ino in table3
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or u

<400> SEQUENCE: 17
uucuagccuu cnggagucag ggc                                              23

<210> SEQ ID NO 18
<211> LENGTH: 52
<212> TYPE: DNA
<213> ORGANISM: Artificial Sequence
<220> FEATURE:
<223> OTHER INFORMATION: HRz1C oligo DNA

<400> SEQUENCE: 18
gcaatacgta ttcgaaaact catcagtcct attgctatag tgagtcgtat ta             52

<210> SEQ ID NO 19
<211> LENGTH: 59
<212> TYPE: DNA
<213> ORGANISM: Artificial Sequence
<220> FEATURE:
<223> OTHER INFORMATION: HRz 2C oligo DNA

<400> SEQUENCE: 19
gcaatacgta ttcggccttt cggcctcatc agtcctattg ctatagtgag tcgtattag      59

<210> SEQ ID NO 20
<211> LENGTH: 53
<212> TYPE: DNA
<213> ORGANISM: Artificial Sequence
<220> FEATURE:
<223> OTHER INFORMATION: HRzC 1E oligo DNA

<400> SEQUENCE: 20
agcaatacgt tcgaaaact catcagatcc tattctatag tgagtcgtat tag             53

<210> SEQ ID NO 21
<211> LENGTH: 59
<212> TYPE: DNA
<213> ORGANISM: Artificial Sequence
<220> FEATURE:
<223> OTHER INFORMATION: HRzC 2E oligo DNA

<400> SEQUENCE: 21
agcaatacgt ttcggccttt cggcctcatc agatcctatt ctatagtgag tcgtattag     59

<210> SEQ ID NO 22
<211> LENGTH: 40
<212> TYPE: DNA
<213> ORGANISM: Artificial Sequence
<220> FEATURE:
<223> OTHER INFORMATION: S oligo DNA

<400> SEQUENCE: 22
caataggatt acgtattgct actatagtga gtcgtattag                           40
```

```
<210> SEQ ID NO 23
<211> LENGTH: 59
<212> TYPE: DNA
<213> ORGANISM: Artificial Sequence
<220> FEATURE:
<223> OTHER INFORMATION: S5 oligo DNA

<400> SEQUENCE: 23
ggctatgctc aataggatta cgtattgcta cataccgatc ctatagtgag tcgtattag      59

<210> SEQ ID NO 24
<211> LENGTH: 19
<212> TYPE: DNA
<213> ORGANISM: Artificial Sequence
<220> FEATURE:
<223> OTHER INFORMATION: T7proG cap

<400> SEQUENCE: 24
ctaatacgac tcactatag                                                  19

<210> SEQ ID NO 25
<211> LENGTH: 29
<212> TYPE: DNA
<213> ORGANISM: Artificial Sequence
<220> FEATURE:
<223> OTHER INFORMATION: Library H(+)

<400> SEQUENCE: 25
ctaatacgac tcactatagg ctatgctca                                       29

<210> SEQ ID NO 26
<211> LENGTH: 59
<212> TYPE: DNA
<213> ORGANISM: Artificial Sequence
<220> FEATURE:
<223> OTHER INFORMATION: Library H1(-)
<220> FEATURE:
<221> NAME/KEY: misc_feature
<222> LOCATION: (19)..(42)
<223> OTHER INFORMATION: n is a, c, g, or t

<400> SEQUENCE: 26
ggtatgtagc aatacgtann nnnnnnnnnn nnnnnnnnnn nntcctattg agcatagcc      59

<210> SEQ ID NO 27
<211> LENGTH: 63
<212> TYPE: DNA
<213> ORGANISM: Artificial Sequence
<220> FEATURE:
<223> OTHER INFORMATION: Library H2(-)
<220> FEATURE:
<221> NAME/KEY: misc_feature
<222> LOCATION: (19)..(42)
<223> OTHER INFORMATION: n is a, c, g, or t
<220> FEATURE:
<221> NAME/KEY: misc_feature
<222> LOCATION: (49)..(52)
<223> OTHER INFORMATION: n is a, c, g, or t

<400> SEQUENCE: 27
ggtatgtagc aatacgtann nnnnnnnnnn nnnnnnnnnn nntcctatnn nntgagcata     60
gcc                                                                   63

<210> SEQ ID NO 28
<211> LENGTH: 29
<212> TYPE: DNA
<213> ORGANISM: Artificial Sequence
```

```
<220> FEATURE:
<223> OTHER INFORMATION: Library H(+)

<400> SEQUENCE: 28
ctaatacgac tcactatagg ctatgctca                                          29

<210> SEQ ID NO 29
<211> LENGTH: 16
<212> TYPE: DNA
<213> ORGANISM: Artificial Sequence
<220> FEATURE:
<223> OTHER INFORMATION: Selection H RT

<400> SEQUENCE: 29
ggtatgtagc aatacg                                                        16

<210> SEQ ID NO 30
<211> LENGTH: 26
<212> TYPE: DNA
<213> ORGANISM: Artificial Sequence
<220> FEATURE:
<223> OTHER INFORMATION: HHSeq_F_EcoRI

<400> SEQUENCE: 30
cggaattcta atacgactca ctatag                                             26

<210> SEQ ID NO 31
<211> LENGTH: 25
<212> TYPE: DNA
<213> ORGANISM: Artificial Sequence
<220> FEATURE:
<223> OTHER INFORMATION: HHSeq_R_BamHI

<400> SEQUENCE: 31
gcgggatccg gtatgtagca atacg                                              25

<210> SEQ ID NO 32
<211> LENGTH: 27
<212> TYPE: RNA
<213> ORGANISM: Artificial Sequence
<220> FEATURE:
<223> OTHER INFORMATION: Biotinized RNA

<400> SEQUENCE: 32
cauuacguaa uccuauugag cauagcc                                            27

<210> SEQ ID NO 33
<211> LENGTH: 35
<212> TYPE: RNA
<213> ORGANISM: Artificial Sequence
<220> FEATURE:
<223> OTHER INFORMATION: Chem.14

<400> SEQUENCE: 33
gaauaggauc ugaugaguuu ucgaaacgua uugcu                                   35

<210> SEQ ID NO 34
<211> LENGTH: 41
<212> TYPE: RNA
<213> ORGANISM: Artificial Sequence
<220> FEATURE:
<223> OTHER INFORMATION: Chem.15

<400> SEQUENCE: 34
gaauaggauc ugaugaggcc gaaaggccga aacguauugc u                            41
```

```
<210> SEQ ID NO 35
<211> LENGTH: 35
<212> TYPE: RNA
<213> ORGANISM: Artificial Sequence
<220> FEATURE:
<223> OTHER INFORMATION: Chem.16

<400> SEQUENCE: 35
gcaauaggac ugaugaguuu ucgaauacgu auugc                              35

<210> SEQ ID NO 36
<211> LENGTH: 41
<212> TYPE: RNA
<213> ORGANISM: Artificial Sequence
<220> FEATURE:
<223> OTHER INFORMATION: Chem.17

<400> SEQUENCE: 36
gcaauaggac ugaugaggcc gaaaggccga auacguauug c                       41

<210> SEQ ID NO 37
<211> LENGTH: 59
<212> TYPE: RNA
<213> ORGANISM: Artificial Sequence
<220> FEATURE:
<223> OTHER INFORMATION: Library H1 in figure13
<220> FEATURE:
<221> NAME/KEY: misc_feature
<222> LOCATION: (18)..(41)
<223> OTHER INFORMATION: n is a, c, g, or u

<400> SEQUENCE: 37
ggcuaugcuc aauaggannn nnnnnnnnnn nnnnnnnnnn nuacguauug cuacauacc    59

<210> SEQ ID NO 38
<211> LENGTH: 63
<212> TYPE: RNA
<213> ORGANISM: Artificial Sequence
<220> FEATURE:
<223> OTHER INFORMATION: Library H2 in figure14
<220> FEATURE:
<221> NAME/KEY: misc_feature
<222> LOCATION: (12)..(15)
<223> OTHER INFORMATION: n is a, c, g, or u
<220> FEATURE:
<221> NAME/KEY: misc_feature
<222> LOCATION: (22)..(45)
<223> OTHER INFORMATION: n is a, c, g, or u

<400> SEQUENCE: 38
ggcuaugcuc annnnauagg annnnnnnnn nnnnnnnnnn nnnnnuacgu auugcuacau   60
acc                                                                 63

<210> SEQ ID NO 39
<211> LENGTH: 41
<212> TYPE: RNA
<213> ORGANISM: Artificial Sequence
<220> FEATURE:
<223> OTHER INFORMATION: HR-HTR2C in fugire18

<400> SEQUENCE: 39
gaauaggauc ugaugaggcc gaaaggccga aacguauugc u                       41

<210> SEQ ID NO 40
<211> LENGTH: 41
<212> TYPE: RNA
<213> ORGANISM: Artificial Sequence
```

```
<220> FEATURE:
<223> OTHER INFORMATION: HR-HTR2C-edit in figure18

<400> SEQUENCE: 40
gaauaggacc ugaugaggcc gaaaggccga aacguauugc u                 41

<210> SEQ ID NO 41
<211> LENGTH: 59
<212> TYPE: RNA
<213> ORGANISM: Artificial Sequence
<220> FEATURE:
<223> OTHER INFORMATION: H1-8-09 in figure13

<400> SEQUENCE: 41
ggcuaugcuc aauaggaucu gaagaguuaa uaaacgaaac guacguauug cuacauacc    59

<210> SEQ ID NO 42
<211> LENGTH: 59
<212> TYPE: RNA
<213> ORGANISM: Artificial Sequence
<220> FEATURE:
<223> OTHER INFORMATION: H1-8-15 in figure13

<400> SEQUENCE: 42
ggcuaugcuc auuaggaucu gaagaguaca ccacgaaacg uugcguauug cuacauacc    59

<210> SEQ ID NO 43
<211> LENGTH: 56
<212> TYPE: RNA
<213> ORGANISM: Artificial Sequence
<220> FEATURE:
<223> OTHER INFORMATION: H1-8-03 in figure13

<400> SEQUENCE: 43
ggcuaugcuc aauaggaucu gaugaguaca acgaaacgua cguauugcua cauacc       56

<210> SEQ ID NO 44
<211> LENGTH: 56
<212> TYPE: RNA
<213> ORGANISM: Artificial Sequence
<220> FEATURE:
<223> OTHER INFORMATION: H1-8-14 in figure13

<400> SEQUENCE: 44
ggcuaugcuc aauaggaucu gaugaguaca acgaaacgug cguauugcua cauacc       56

<210> SEQ ID NO 45
<211> LENGTH: 27
<212> TYPE: RNA
<213> ORGANISM: Artificial Sequence
<220> FEATURE:
<223> OTHER INFORMATION: H1-8-01 in figure13

<400> SEQUENCE: 45
ggcuaugcuc acguauugcu acauacc                                 27

<210> SEQ ID NO 46
<211> LENGTH: 63
<212> TYPE: RNA
<213> ORGANISM: Artificial Sequence
<220> FEATURE:
<223> OTHER INFORMATION: Library H2 in figure14
<220> FEATURE:
<221> NAME/KEY: misc_feature
<222> LOCATION: (12)..(15)
<223> OTHER INFORMATION: n is a, c, g, or u
```

```
<220> FEATURE:
<221> NAME/KEY: misc_feature
<222> LOCATION: (22)..(45)
<223> OTHER INFORMATION: n is a, c, g, or u

<400> SEQUENCE: 46
ggcuaugcuc annnnauagg annnnnnnnn nnnnnnnnnn nnnnnuacgu auugcuacau    60
acc                                                                 63

<210> SEQ ID NO 47
<211> LENGTH: 63
<212> TYPE: RNA
<213> ORGANISM: Artificial Sequence
<220> FEATURE:
<223> OTHER INFORMATION: H2-8-20 in figure14

<400> SEQUENCE: 47
ggcuaugcuc accgaauagg acacacacaa cggugaguau ccagguacgu auugcuacau    60
acc                                                                 63

<210> SEQ ID NO 48
<211> LENGTH: 61
<212> TYPE: RNA
<213> ORGANISM: Artificial Sequence
<220> FEATURE:
<223> OTHER INFORMATION: H2-8-24 in figure14

<400> SEQUENCE: 48
ggcuaugcuc agaugauagg accccaacuc cggcaccuac acugacguau ugcuacauac    60
c                                                                   61

<210> SEQ ID NO 49
<211> LENGTH: 63
<212> TYPE: RNA
<213> ORGANISM: Artificial Sequence
<220> FEATURE:
<223> OTHER INFORMATION: H2-8-09 in figure14

<400> SEQUENCE: 49
ggcuaugcuc acauaauagg acuaauuguc aaacccuuuu uaugugacgu auugcuacau    60
acc                                                                 63

<210> SEQ ID NO 50
<211> LENGTH: 63
<212> TYPE: RNA
<213> ORGANISM: Artificial Sequence
<220> FEATURE:
<223> OTHER INFORMATION: H2-8-06 in figure14

<400> SEQUENCE: 50
ggcuaugcuc agacccuagg aaccaaacaa auacccgaaa cgucugacgu auugcuacau    60
acc                                                                 63

<210> SEQ ID NO 51
<211> LENGTH: 63
<212> TYPE: RNA
<213> ORGANISM: Artificial Sequence
<220> FEATURE:
<223> OTHER INFORMATION: H2-8-15 in figure14
```

```
<400> SEQUENCE: 51
ggcuaugcuc auggcagagg agacaccaaa cuaccgagac accaugacgu auugcuacau      60
acc                                                                    63

<210> SEQ ID NO 52
<211> LENGTH: 63
<212> TYPE: RNA
<213> ORGANISM: Artificial Sequence
<220> FEATURE:
<223> OTHER INFORMATION: H2-8-23 in figure14

<400> SEQUENCE: 52
ggcuaugcuc acgacaaagg aaaagaacuu cgcccccuac cccgugacgu auugcuacau      60
acc                                                                    63

<210> SEQ ID NO 53
<211> LENGTH: 62
<212> TYPE: RNA
<213> ORGANISM: Artificial Sequence
<220> FEATURE:
<223> OTHER INFORMATION: H2-8-12 in figure14

<400> SEQUENCE: 53
ggcuaugcuc acgugauaga acaaaaugca ccacaaccccc acgugacgua uugcuacaua     60
cc                                                                     62

<210> SEQ ID NO 54
<211> LENGTH: 62
<212> TYPE: RNA
<213> ORGANISM: Artificial Sequence
<220> FEATURE:
<223> OTHER INFORMATION: H2-8-19 in figure14

<400> SEQUENCE: 54
ggcuugcuca accgagagga agagcaaaaa cauacgacga ucugugcgua uugcuacaua      60
cc                                                                     62

<210> SEQ ID NO 55
<211> LENGTH: 63
<212> TYPE: RNA
<213> ORGANISM: Artificial Sequence
<220> FEATURE:
<223> OTHER INFORMATION: H2-8-07 in figure14

<400> SEQUENCE: 55
ggcuaugcuc augaaauagg acaaacaaac cucaccauuu caugaugcgu auugcuacau      60
acc                                                                    63

<210> SEQ ID NO 56
<211> LENGTH: 63
<212> TYPE: RNA
<213> ORGANISM: Artificial Sequence
<220> FEATURE:
<223> OTHER INFORMATION: H2-8-14 in figure14

<400> SEQUENCE: 56
ggcuaugcuc agguuauagg acccaccaaa agaaacuaga ccugaugcgu auugcuacau      60
acc                                                                    63
```

```
<210> SEQ ID NO 57
<211> LENGTH: 63
<212> TYPE: RNA
<213> ORGANISM: Artificial Sequence
<220> FEATURE:
<223> OTHER INFORMATION: H2-8-16 in figure14

<400> SEQUENCE: 57
ggcuaugcuc acaccauagg accaaccaaa cgaaccgaag ugugaugcgu auugcuacau    60
acc                                                                 63

<210> SEQ ID NO 58
<211> LENGTH: 60
<212> TYPE: RNA
<213> ORGANISM: Artificial Sequence
<220> FEATURE:
<223> OTHER INFORMATION: H2-8-02 in figure14

<400> SEQUENCE: 58
ggcuaugcuc agacaaaagg acaaaacuac acccaaaccc ugagcguauu gcuacauacc   60

<210> SEQ ID NO 59
<211> LENGTH: 55
<212> TYPE: RNA
<213> ORGANISM: Artificial Sequence
<220> FEATURE:
<223> OTHER INFORMATION: H2-8-05 in figure14

<400> SEQUENCE: 59
ggcuaugcuc agaugauaag acaaaacccg aauccugagc guauugcuac auacc        55

<210> SEQ ID NO 60
<211> LENGTH: 57
<212> TYPE: RNA
<213> ORGANISM: Artificial Sequence
<220> FEATURE:
<223> OTHER INFORMATION: H2-8-03 in figure14

<400> SEQUENCE: 60
ggcuaugcuc accaaauaag aaaccaaaac cuaaaaguga gcguauugcu acauacc      57

<210> SEQ ID NO 61
<211> LENGTH: 57
<212> TYPE: RNA
<213> ORGANISM: Artificial Sequence
<220> FEATURE:
<223> OTHER INFORMATION: H2-8-04 in figure14

<400> SEQUENCE: 61
ggcuaugcuc accaaauaag aaaccaaaac cuaaaaauga gcguauugcu acauacc      57

<210> SEQ ID NO 62
<211> LENGTH: 58
<212> TYPE: RNA
<213> ORGANISM: Artificial Sequence
<220> FEATURE:
<223> OTHER INFORMATION: H2-8-10 in figure14

<400> SEQUENCE: 62
ggcuaugcuc acccaaauaa gaaaccaaaa ccuaaaagug agcguauugc uacauacc     58

<210> SEQ ID NO 63
<211> LENGTH: 63
<212> TYPE: RNA
<213> ORGANISM: Artificial Sequence
```

```
<220> FEATURE:
<223> OTHER INFORMATION: H2-01 in figure15

<400> SEQUENCE: 63
ggcuaugcuc aggaaauaag aacuaaaaau ccccaaaaac cugaguacgu auugcuacau      60
acc                                                                   63

<210> SEQ ID NO 64
<211> LENGTH: 63
<212> TYPE: RNA
<213> ORGANISM: Artificial Sequence
<220> FEATURE:
<223> OTHER INFORMATION: H2-06 in figure15

<400> SEQUENCE: 64
ggcuaugcuc accuaauaga aaaucccaaa acaucuagau aaagugacgu auugcuacau      60
acc                                                                   63

<210> SEQ ID NO 65
<211> LENGTH: 63
<212> TYPE: RNA
<213> ORGANISM: Artificial Sequence
<220> FEATURE:
<223> OTHER INFORMATION: H2-37 in figure15

<400> SEQUENCE: 65
ggcuaugcuc aggaaauagg agcugacaaa gcaaaccuac cugaguacgu auugcuacau      60
acc                                                                   63

<210> SEQ ID NO 66
<211> LENGTH: 28
<212> TYPE: RNA
<213> ORGANISM: Artificial Sequence
<220> FEATURE:
<223> OTHER INFORMATION: ApoB-uri in figure20

<400> SEQUENCE: 66
gcagacauau augauauaau uugaucag                                        28

Figure 21:
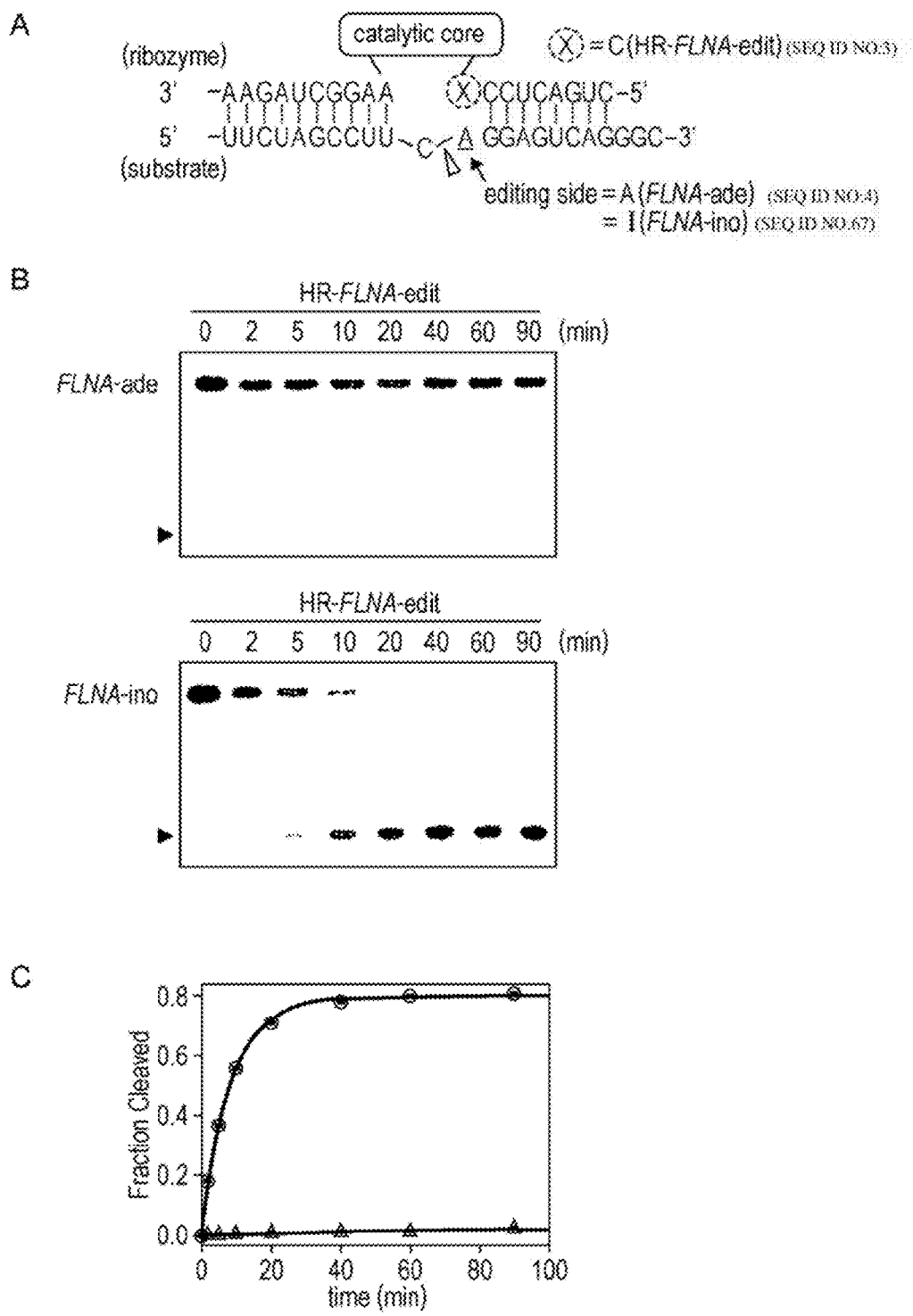
FIG. 21 shows the results of cleavage reactions over time and kinetic analysis of HR-APOB to edited and unedited APOB mRNA fragments under single turnover conditions in FIG. 20.

<210> SEQ ID NO 67
<211> LENGTH: 23
<212> TYPE: RNA
<213> ORGANISM: Artificial Sequence
<220> FEATURE:
<223> OTHER INFORMATION: FLNA-ino in figure21
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or u

<400> SEQUENCE: 67
uucuagccuu cnggagucag ggc                                             23

<210> SEQ ID NO 68
<211> LENGTH: 17
<212> TYPE: RNA
<213> ORGANISM: HUMAN

<400> SEQUENCE: 68
agcaauacgu aauccua                                                    17
```

The invention claimed is:
1. A method for the cleavage of a target RNA comprising:
reacting a member selected from the group consisting of a hammerhead ribozyme represented by the formula of SEQ ID NO. 1:

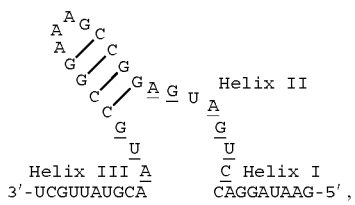

a hammerhead ribozyme represented by the formula of SEQ ID NO. 3:

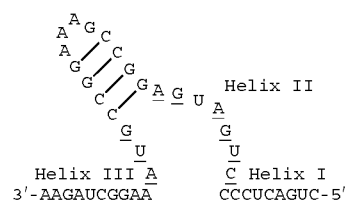

and a hammerhead ribozyme represented by the formula of SEQ ID NO. 5:

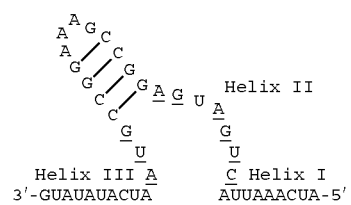

with a member selected from the group consisting of a target RNA represented by formula:
5'-GGAUCGGUAUGUAGCAAUACGU-A-AUCCUAUUGAGCAUGCC-3' (SEQ ID NO:2), a target RNA represented by formula:
5'-UUCUAGCCUU-C-AGGAGUCAGGGC-3' (SEQ ID NO:4) and a target RNA represented by formula:
5'-GCAGACAUAUAUGAU-A-CAAUUUGAUCAG-3' (SEQ ID NO:6), respectively, to give a hammerhead ribozyme-target RNA construct represented by the formula of SEQ ID NOs. 1 and 2[IIIb]:

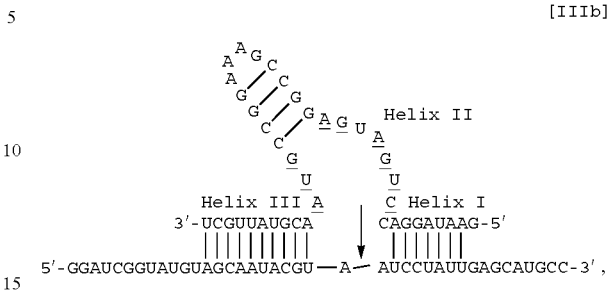

a hammerhead ribozyme-target RNA construct represented by the formula of SEQ ID NOs. 3 and 4[IIIc]:

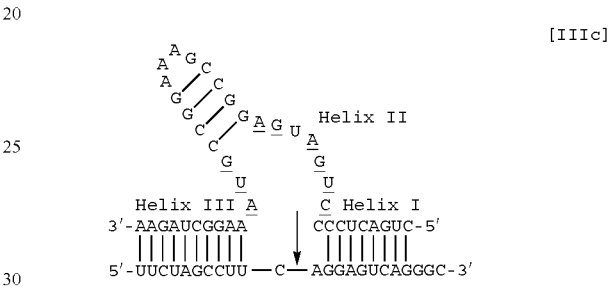

and
a hammerhead ribozyme-target RNA construct represented by the formula of SEQ ID NOs. 5 and 6 [IIId]:

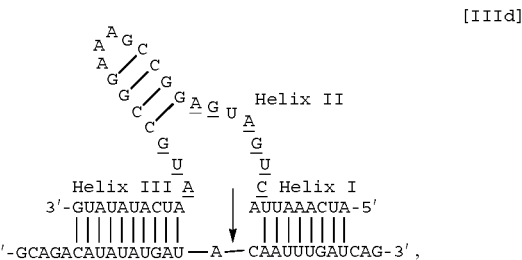

wherein arrowhead symbol means a cleaving site.

* * * * *